United States Patent
Estes et al.

(10) Patent No.: US 8,870,853 B2
(45) Date of Patent: Oct. 28, 2014

(54) OPERATING A PORTABLE MEDICAL DEVICE

(75) Inventors: Mark C. Estes, Malibu, CA (US); Mitchell Wenger, Ross, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 168 days.

(21) Appl. No.: 13/344,836

(22) Filed: Jan. 6, 2012

(65) Prior Publication Data

US 2012/0109100 A1    May 3, 2012

Related U.S. Application Data

(63) Continuation of application No. 12/781,450, filed on May 17, 2010, now Pat. No. 8,109,921, which is a continuation of application No. 11/851,194, filed on Sep. 6, 2007, now Pat. No. 7,717,903.

(51) Int. Cl.
| | |
|---|---|
| *A61K 9/22* | (2006.01) |
| *G06F 19/00* | (2011.01) |
| *A61M 5/142* | (2006.01) |
| *A61M 5/168* | (2006.01) |
| *A61M 5/145* | (2006.01) |
| *A61M 5/172* | (2006.01) |
| *A61M 5/315* | (2006.01) |

(52) U.S. Cl.
CPC ....... *G06F 19/3412* (2013.01); *A61M 5/14244* (2013.01); *A61M 5/16804* (2013.01); *G06F 19/3468* (2013.01); *A61M 5/14526* (2013.01); *A61M 5/1723* (2013.01); *A61M 2005/14268* (2013.01); *A61M 2005/31518* (2013.01)
USPC ..................................... 604/890.1

(58) Field of Classification Search
USPC ...................................... 604/890.1
See application file for complete search history.

(56) References Cited

U.S. PATENT DOCUMENTS

| | | | |
|---|---|---|---|
| 2,605,765 | A | 8/1952 | Kollsman |
| 3,886,938 | A | 6/1975 | Szabo et al. |
| 4,077,405 | A | 3/1978 | Haerten et al. |
| 4,231,368 | A | 11/1980 | Becker |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

Medtronic News Release, "Medtronic Receives FDA Approval for World's First Insulin Pump with Real-time Continuous Glucose Monitoring," Apr. 13, 2006, 3 pages.

(Continued)

*Primary Examiner* — Nicholas Lucchesi
*Assistant Examiner* — Diva K Chander
(74) *Attorney, Agent, or Firm* — Fish & Richardson P.C.

(57) ABSTRACT

Some embodiments of a portable medical device, such as an infusion pump, can receive an external reference signal (e.g., a radio, cellular and/or satellite signal) to provide an automatic time-setting and maintenance operation. In these circumstances, the medical device can maintain accurate time and date information even in the event of a power interruption, a time-zone change and/or an internal clock error, for example. In this manner, the portable medical device provides safe operation and added convenience to the user.

49 Claims, 13 Drawing Sheets

(56) References Cited

U.S. PATENT DOCUMENTS

| | | |
|---|---|---|
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon |
| 5,314,412 A | 5/1994 | Rex |
| 5,335,994 A | 8/1994 | Weynant nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell |
| 5,549,117 A * | 8/1996 | Tacklind et al. ............... 600/529 |
| 5,551,850 A * | 9/1996 | Williamson et al. ........... 417/474 |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,458,102 B1 | 10/2002 | Mann et al. |
| 6,461,331 B1 | 10/2002 | Van Antwerp |
| 6,474,219 B2 | 11/2002 | Klitmose et al. |
| 6,485,461 B1 * | 11/2002 | Mason et al. ................. 604/132 |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 * | 4/2003 | Simonsen et al. ............ 600/300 |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 * | 12/2003 | Gregory et al. ............... 604/131 |
| 6,656,159 B2 * | 12/2003 | Flaherty ........................ 604/131 |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |

(56) References Cited

U.S. PATENT DOCUMENTS

| | | | |
|---|---|---|---|
| 7,018,360 B2 | 3/2006 | Flaherty et al. | |
| 7,025,743 B2 * | 4/2006 | Mann et al. | 604/66 |
| 7,029,455 B2 | 4/2006 | Flaherty | |
| 7,054,836 B2 | 5/2006 | Christensen et al. | |
| 7,104,972 B2 | 9/2006 | Møller et al. | |
| 7,128,727 B2 * | 10/2006 | Flaherty et al. | 604/131 |
| 7,133,329 B2 | 11/2006 | Skyggebjerg et al. | |
| 7,232,423 B2 | 6/2007 | Mernoe et al. | |
| 7,278,983 B2 * | 10/2007 | Ireland et al. | 604/66 |
| 7,911,326 B2 * | 3/2011 | Sutardja | 340/12.32 |
| 2001/0056262 A1 | 12/2001 | Cabiri et al. | |
| 2002/0004651 A1 | 1/2002 | Ljndggreen et al. | |
| 2002/0007154 A1 | 1/2002 | Hansen et al. | |
| 2002/0040208 A1 * | 4/2002 | Flaherty et al. | 604/288.01 |
| 2002/0091358 A1 | 7/2002 | Klitmose | |
| 2002/0126036 A1 | 9/2002 | Flaherty et al. | |
| 2002/0147135 A1 | 10/2002 | Schnell | |
| 2002/0169439 A1 | 11/2002 | Flaherty et al. | |
| 2003/0050621 A1 | 3/2003 | Lebel et al. | |
| 2003/0055380 A1 | 3/2003 | Flaherty | |
| 2003/0065308 A1 | 4/2003 | Lebel et al. | |
| 2003/0088238 A1 | 5/2003 | Poulsen | |
| 2003/0167035 A1 | 9/2003 | Flaherty et al. | |
| 2003/0199825 A1 | 10/2003 | Flaherty | |
| 2003/0216683 A1 | 11/2003 | Shekalim | |
| 2004/0010207 A1 | 1/2004 | Flaherty et al. | |
| 2004/0019325 A1 | 1/2004 | Shekalim | |
| 2004/0064088 A1 | 4/2004 | Gorman et al. | |
| 2004/0064096 A1 | 4/2004 | Flaherty et al. | |
| 2004/0078028 A1 | 4/2004 | Flaherty et al. | |
| 2004/0087894 A1 | 5/2004 | Flaherty | |
| 2004/0092865 A1 | 5/2004 | Flaherty et al. | |
| 2004/0092878 A1 | 5/2004 | Flaherty | |
| 2004/0116866 A1 | 6/2004 | Gorman et al. | |
| 2004/0127844 A1 | 7/2004 | Flaherty | |
| 2004/0153032 A1 | 8/2004 | Garribotto et al. | |
| 2004/0171983 A1 | 9/2004 | Sparks et al. | |
| 2004/0176727 A1 | 9/2004 | Shekalim | |
| 2004/0204673 A1 | 10/2004 | Flaherty | |
| 2004/0215492 A1 * | 10/2004 | Choi | 705/2 |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0021005 A1 | 1/2005 | Flaherty et al. | |
| 2005/0022274 A1 | 1/2005 | Campbell et al. | |
| 2005/0065760 A1 | 3/2005 | Murtfeldt et al. | |
| 2005/0090808 A1 | 4/2005 | Malave et al. | |
| 2005/0095063 A1 | 5/2005 | Fathallah et al. | |
| 2005/0154271 A1 * | 7/2005 | Rasdal et al. | 600/347 |
| 2005/0160858 A1 | 7/2005 | Mernoe | |
| 2005/0171512 A1 | 8/2005 | Flaherty | |
| 2005/0182366 A1 | 8/2005 | Vogt et al. | |
| 2005/0192561 A1 | 9/2005 | Mernoe | |
| 2005/0203461 A1 | 9/2005 | Flaherty et al. | |
| 2005/0215982 A1 | 9/2005 | Malave et al. | |
| 2005/0222645 A1 | 10/2005 | Malave et al. | |
| 2005/0238507 A1 | 10/2005 | Dilanni et al. | |
| 2005/0245878 A1 | 11/2005 | Mernoe et al. | |
| 2005/0251097 A1 | 11/2005 | Mernoe | |
| 2005/0267402 A1 | 12/2005 | Stewart et al. | |
| 2005/0273059 A1 | 12/2005 | Mernoe et al. | |
| 2006/0041229 A1 | 2/2006 | Garibotto et al. | |
| 2006/0069382 A1 | 3/2006 | Pedersen | |
| 2006/0074381 A1 | 4/2006 | Malave et al. | |
| 2006/0095014 A1 | 5/2006 | Ethelfeld | |
| 2006/0135913 A1 | 6/2006 | Ethelfeld | |
| 2006/0142698 A1 | 6/2006 | Ethelfeld | |
| 2006/0178633 A1 | 8/2006 | Garibotto et al. | |
| 2006/0184119 A1 | 8/2006 | Remde et al. | |
| 2006/0200073 A1 | 9/2006 | Radmer et al. | |
| 2006/0206054 A1 | 9/2006 | Shekalim | |
| 2006/0247581 A1 | 11/2006 | Pedersen et al. | |
| 2007/0073228 A1 * | 3/2007 | Mernoe et al. | 604/131 |
| 2007/0073236 A1 | 3/2007 | Mernoe et al. | |
| 2007/0106218 A1 | 5/2007 | Yodfat et al. | |
| 2007/0124002 A1 | 5/2007 | Estes et al. | |
| 2007/0142822 A1 * | 6/2007 | Remde | 604/890.1 |
| 2007/0156092 A1 | 7/2007 | Estes et al. | |
| 2007/0167905 A1 | 7/2007 | Estes et al. | |
| 2007/0167912 A1 | 7/2007 | Causey et al. | |
| 2007/0186923 A1 * | 8/2007 | Poutiatine et al. | 128/200.14 |
| 2007/0255250 A1 | 11/2007 | Moberg et al. | |
| 2008/0161754 A1 | 7/2008 | Marano-Ford | |

FOREIGN PATENT DOCUMENTS

| | | |
|---|---|---|
| DE | 102 36 669 | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 00/29047 | 5/2000 |
| WO | WO 01/72360 | 10/2001 |
| WO | WO 01/91822 | 12/2001 |
| WO | WO 01/91833 | 12/2001 |
| WO | WO 02/040083 | 5/2002 |
| WO | WO 02/057627 | 7/2002 |
| WO | WO 02/100469 | 12/2002 |
| WO | WO 03/103763 | 12/2003 |
| WO | WO 04/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Patent Abstracts of Japan, vol. 1999, No. 04, and JP 11 010036 , Apr. 30, 1999 and Jan. 19, 1999, Toray Ind. Inc.

International Search Report & Written Opinion, PCT/US2008/069624, mailed Oct. 20, 2008, 19 pages.

* cited by examiner

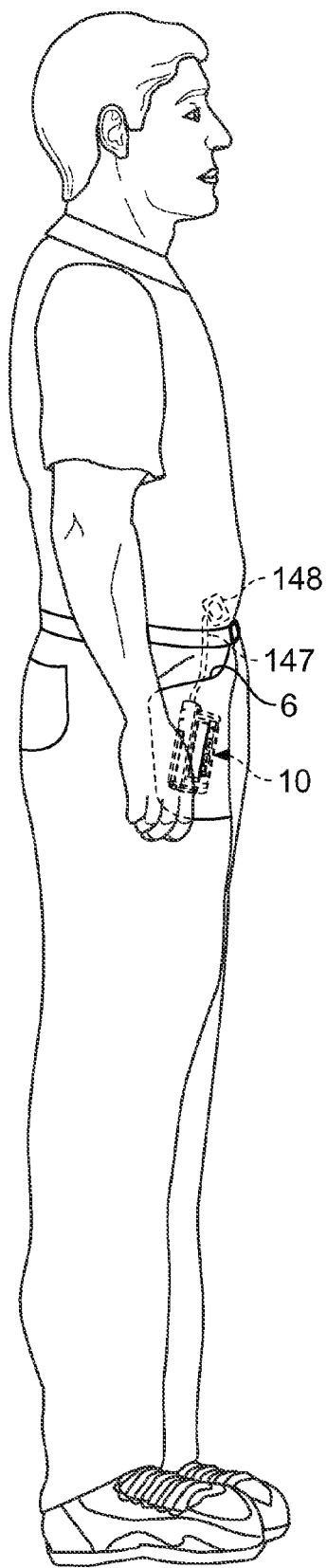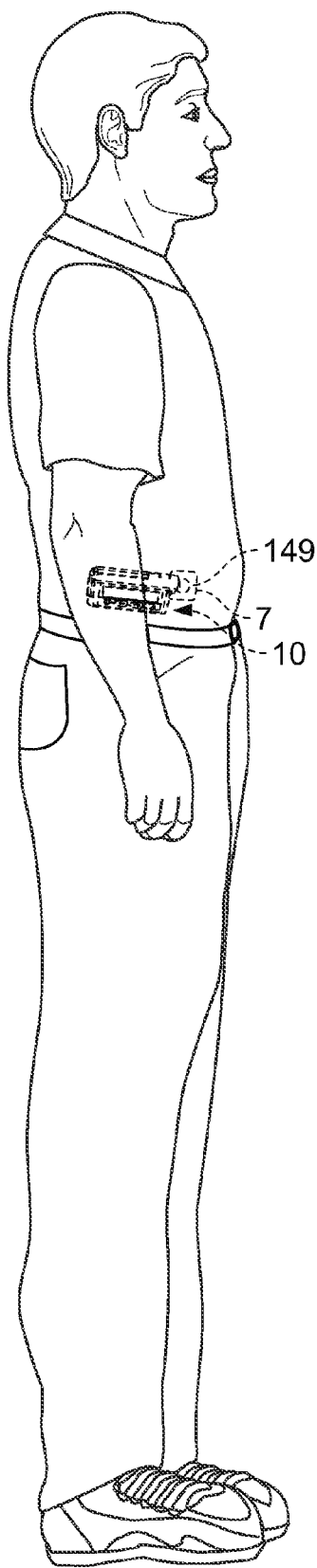

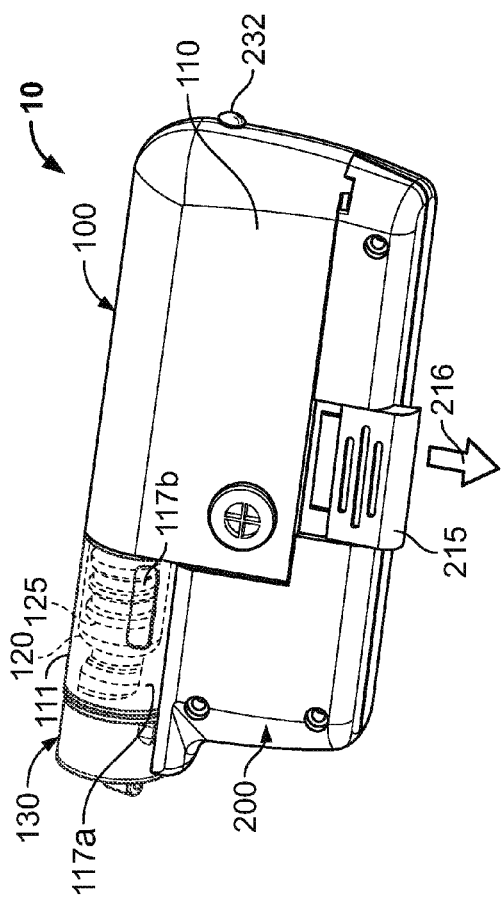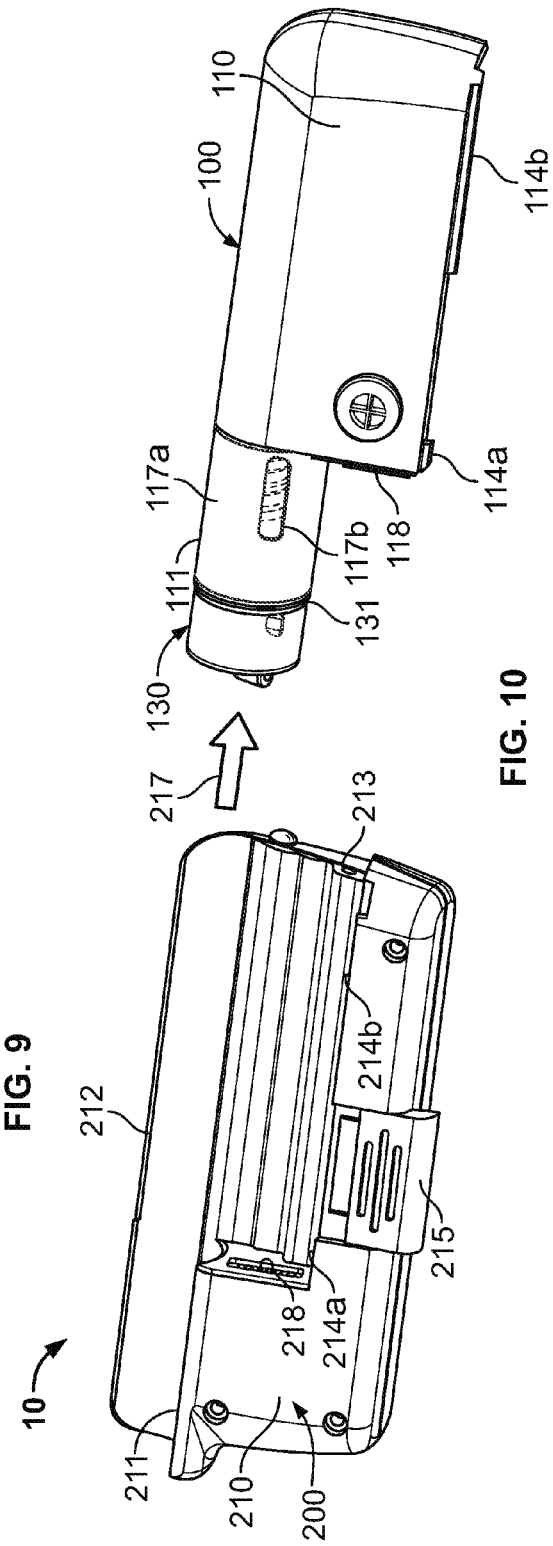

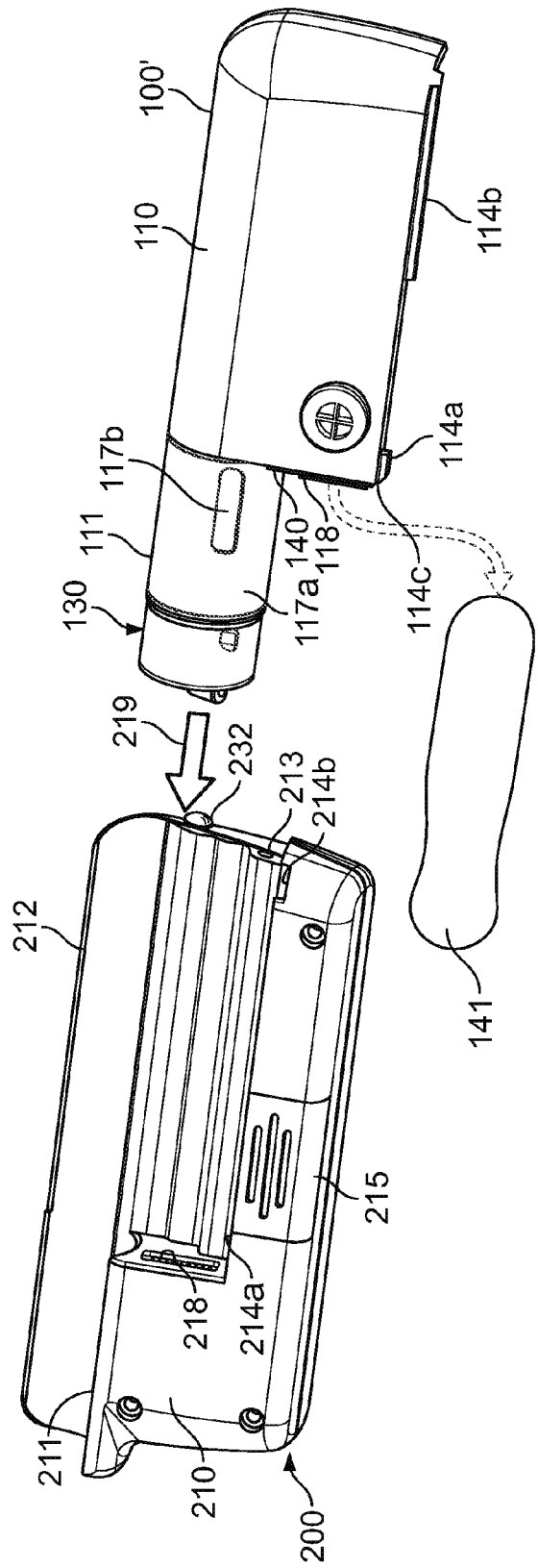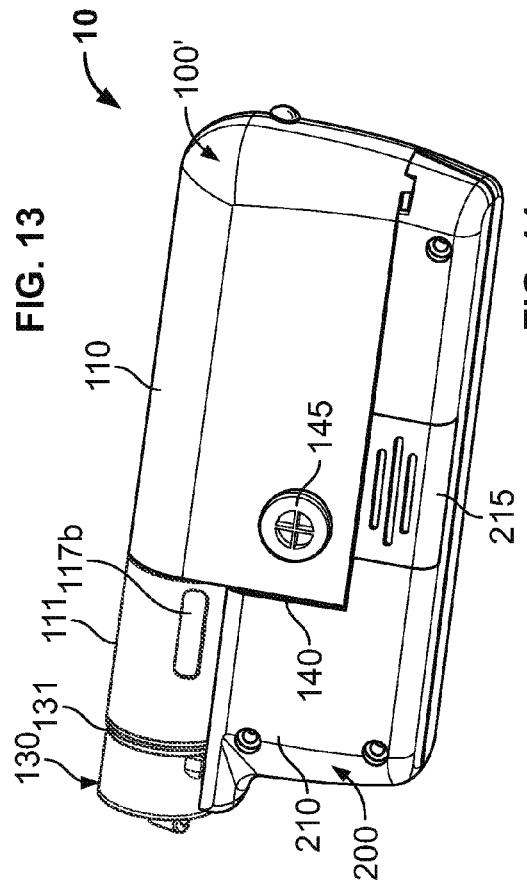
FIG. 13
FIG. 14

OPERATING A PORTABLE MEDICAL DEVICE

CROSS-REFERENCE TO RELATED APPLICATION(S)

This application is a continuation of U.S. patent application Ser. No. 12/781,450, filed on May 17, 2010 by Estes et al., which is a continuation of U.S. patent application Ser. No. 11/851,194, filed on Sep. 6, 2007 by Estes et al., the contents of which are fully incorporated herein by reference.

TECHNICAL FIELD

This document relates to operating a medical device, such as an infusion pump to dispense a medicine.

BACKGROUND

Medical devices are commonly implemented to provide medical treatment to a patient. Pump devices, for example, are commonly used to deliver one or more fluids to a targeted individual. As one specific example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels. Such treatment plans include scheduled dosages of a particular medicine. The dosage amounts can vary depending upon the time of day.

SUMMARY

Some embodiments of a portable medical device for treatment of diabetes, such as an infusion pump or a glucose monitoring system, can receive an external reference signal (e.g., a radio, cellular and/or satellite signal) to provide an automatic time-setting and maintenance operation. In these circumstances, the medical device can maintain accurate time and date information even in the event of a power interruption, a time-zone change and/or an internal clock error, for example. In this manner, the portable medical device provides safe operation and added convenience to the user.

Some embodiments of a method of operating a portable medical device include receiving an external reference signal from an external reference source, updating at least one of a time setting and date setting of the medical device based on the external reference signal to provide at least one of an updated time and updated date setting and operating the portable medical device based on the external reference signal.

In particular embodiments, a portable medical device assembly include an external reference system that receives an external reference signal from an external reference source and a controller that updates at least one of a time setting and a date setting of the medical device based on the external reference signal to provide at least one of an updated time setting and an updated date setting. The controller operates the portable medical device based on at least one of the updated time setting and the updated date setting.

Certain embodiments of a wearable infusion pump system include a disposable and non-reusable pump device including a drive system to dispense medicine from the pump device, the pump device having a first electrical connector that is externally accessible, a reusable controller device removably attachable to the disposable and non-reusable pump device. Some embodiments of the controller device include a second electrical connector that is engageable with the first connector to provide electrical communication between control circuitry of the controller device and the drive system of the pump device, an external reference system that receives an external reference signal from an external reference source, and a processor that updates at least one of a time setting and a date setting of the infusion pump system based on the external reference signal to provide at least one of an updated time setting and an updated date setting. The reusable controller operates the portable medical device based on at least one of the updated time setting and the updated date setting.

Some or all of the embodiments described herein may provide one or more of the following advantages. First, an internal reference time set and/or updated by an external time signal to maintain accurate time and date information even in the event of a power interruption. For example, power may be removed during a battery change and/or the battery may deplete over time. Upon re-powering, the external reference system automatically communicates with the remote time and date reference source and immediately and accurately updates the internal reference time and date. In this manner, the system can reduce the risk of the reference time either not being updated or not being accurately updated by the user. Furthermore, the accuracy of the internal reference time is maintained throughout the operation of the medical device.

Secondly, the infusion pump system that incorporates the external reference system can be implemented to automatically adjust the dosing schedule in the case of a time change. More specifically, in the case of daylight savings time and/or travel between time zones, a time change may occur, which may be several hours or even an entire day. The patient may be alerted to such time changes and may be assisted in adapting the dosing schedule to the new time zone.

Thirdly, the use of the medical device is simplified for the patient. More specifically, the patient is not required to manually set the date and time. As a result, any inaccuracies that may otherwise arise from manually setting the date and time are avoided. Furthermore, the user is not necessarily required to learn how to perform manual setting of the time and date.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 is a perspective view of the infusion pump system of FIG. 6 worn on clothing of a user.

FIG. 8 is a perspective view of an infusion pump system worn on skin of a user, in accordance with particular embodiments.

FIGS. 9 and 10 are perspective views of a pump device being detached from a controller device, in accordance with some embodiments.

FIGS. 13 and 14 are perspective views of the pump device of FIG. 11 being attached to the controller device of FIG. 11.

Like reference symbols in the various drawings indicate like elements.

DETAILED DESCRIPTION OF ILLUSTRATIVE EMBODIMENTS

Figure 1:
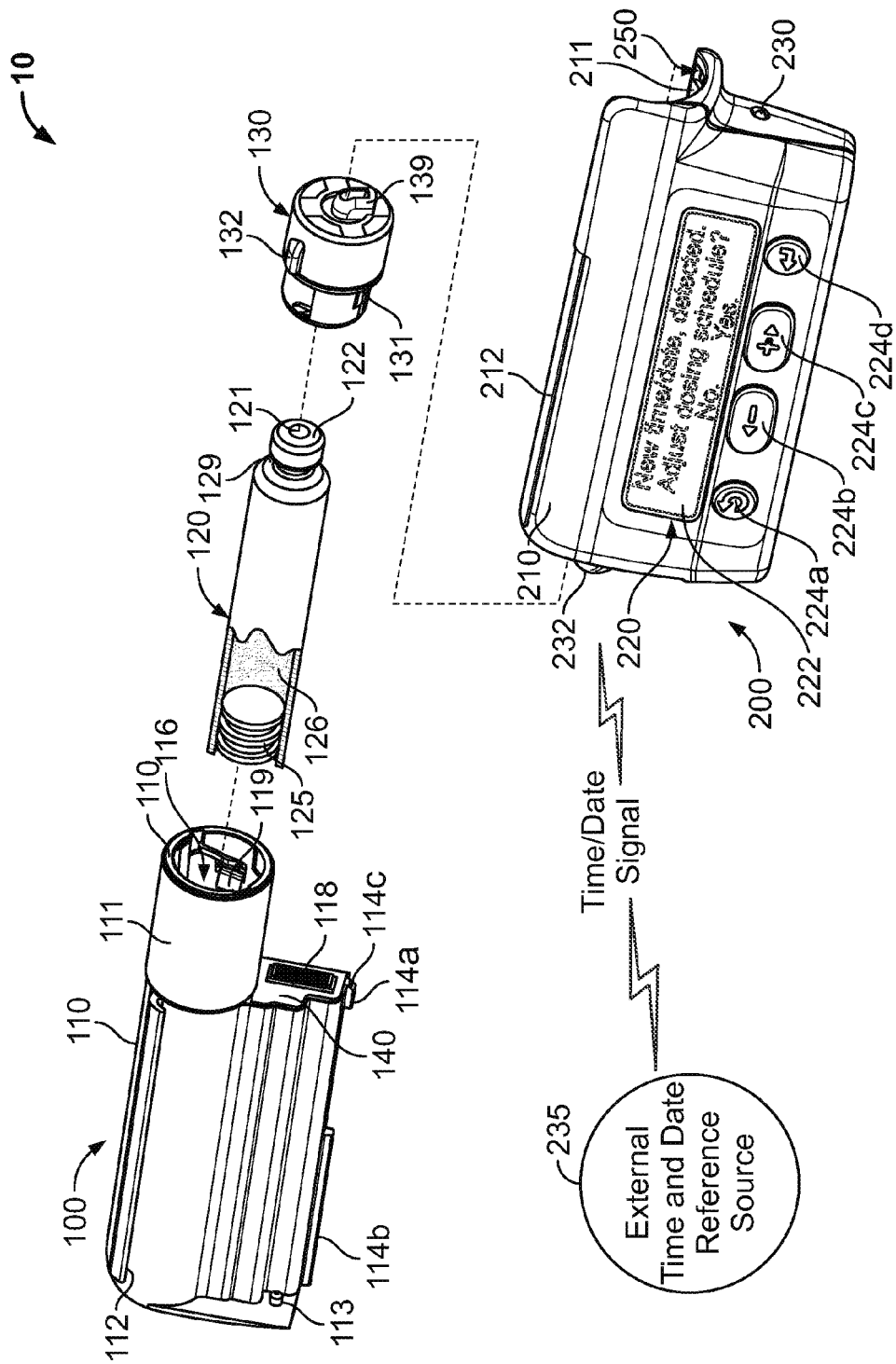
FIG. 1 is a perspective view of an exemplary medical device in the form of an infusion pump system in accordance with some embodiments.
Figure 2:
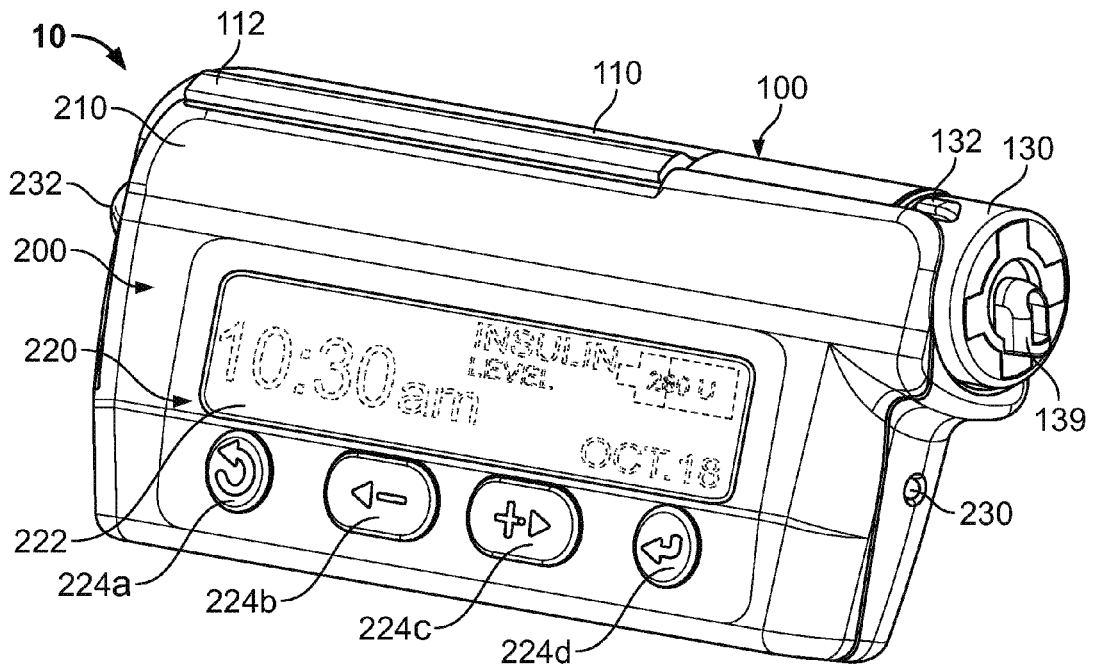
FIG. 2 is a perspective view of the infusion pump system of FIG. 1 in an assembled state.
Figure 3:
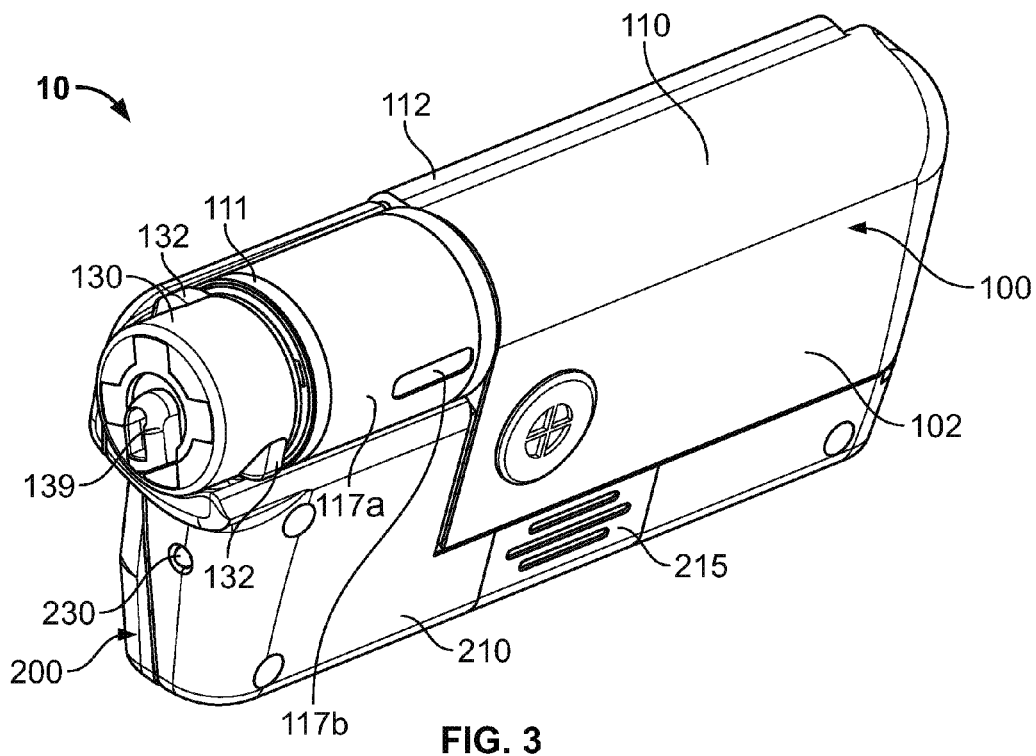
FIG. 3 is another perspective view of the infusion pump system of FIG. 2.

Referring to FIGS. 1-3, an exemplary medical device is provided as a portable infusion pump system 10 that is configured to controllably dispense a medicine to a patient. Although the exemplary medical device is described as a medical infusion pump system 10, it is appreciated that the automatic time and date setting and maintenance features described herein can be implemented in other medical devices, such as blood glucose meters and continuous blood glucose monitors (described in more detail below in connection with FIG. 18).

The infusion pump system 10 can include a pump device 100 and a controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below in connection with FIG. 17) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump system 10 can provide enhanced user safety as a new pump device 100 (and drive system therein) is employed with each new fluid cartridge 120.

Briefly, in use, the infusion pump system 10 is configured to receive an external signal from a remote time and date reference source 235 (e.g., a radio transmitter, a satellite, another broadcast source or the like) to provide automatic time-setting capabilities and related maintenance features. For example, the controller device 200 may include a receiver 232 (FIG. 1) and external reference circuitry (FIG. 15) that can be used to receive the external reference signal, which provides time and/or date information. The controller device 200 can use this information to automatically update the time and date settings and thereafter provide accurately timed delivery of the infused medication, accurately time-stamped data storage, and other features convenient to the user. Such embodiments are described in more detail below in connection with FIGS. 15-16.

In addition, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 includes a housing 210 having a number of features that mate with complementary features of the pump housing 110. In such circumstances, the controller device 200 can removably attach with the pump device 100 in a generally side-by-side configuration while not fully surrounding the pump housing 110. Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable (as described below in connection with FIGS. 6-8). Moreover, at least one of the pump device 100 or the controller device 200 may include a release member that facilitates an easy-to-use detachment and replacement process. For example, as described in more detail below in connection with FIGS. 11-16, an exhausted pump device 100 may be a "one time use" component that is discarded after being used, and a new pump device 100' (having a new medicine cartridge 120') can thereafter be attached to the controller device 200.

Moreover, the pump device 100 and the controller device 200 can be mounted to one another so that the assembled system 10 is resistant to migration of external contaminants (e.g., water from precipitation or splashing, sweat, and the like) both into the pump housing structure 110 and the controller housing structure 210. In particular, the infusion pump system 10 may include one or more seals that are arranged to hinder migration of external contaminants into the cavity of the pump device 100 (e.g., to protect the insulin container 120 and the drive system during operation). Also, the infusion pump system may include one or more gaskets arranged proximate to the electrical connection location (between the pump device 100 and the controller device 200) to protect the electrical connection from migration of external contaminants. Thus, in some embodiments, the infusion pump system 10 can be assembled into a water resistant configuration that protects sensitive components from water migration (e.g., if the user encounters water while wearing the pump system 10).

Still referring to FIGS. 1-3, in this embodiment, the medical infusion pump system 10 is configured to controllably dispense a medicine from the cartridge 120. As such, the fluid cartridge 120 may contain a medicine 126 (FIG. 1) to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 1, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 1) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100.

Such a configuration may facilitate the "one-time-use" feature of the pump device 100. Because the retainer wings 119 interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-3, the cap device 130 can be joined with the pump device 100 after the medicine cartridge is inserted in the cavity 116. In this embodiment, the cap device 130 is multifunctional in that it performs a number of functions for the pump device operation. For example, attachment of the cap device 130 may cause one or more of the following preparatory functions: forcing the plunger 125 (FIG. 1) of the fluid cartridge 120 to engage with the piston rod (not shown), piercing a septum 121 of the fluid cartridge 120 to provide a flow path for the fluid, and priming the fluid cartridge 120 with a "break away" force to initiate movement of the plunger 125 in the fluid cartridge 120. In addition or in the alternative, attachment of the cap device 130 may also cause one or more of the following safety related functions: aligning an occlusion sensor with the a portion of the fluid flow path, sealing the pump housing 110 (e.g., using a polymeric o-ring seal 131 or the like) to resist migration of external contaminants into the cavity 116, and ceasing or preventing the dispensation of fluid if the cap device 130 is improperly engaged with the pump housing 110. In other embodiments, the cap device 130 may supplement or replace the previously described retainer wings 119 by locking into position after joining with the pump housing 110, thereby hindering removal of the fluid cartridge 120 in the pump housing 110.

The cap device 130 can include one or more alignment tabs 132 that operate to ensure that the cap device 130 is joined with the pump housing 110 in a selected orientation. For example, as shown in FIGS. 2-3, the cap device 130 may include an output port 139 that connects with tubing (e.g., FIG. 6) for dispensation of the medicine to the user. The output port 139 may have an angled orientation such that a portion of the tubing extends transversely to the central axis of the cartridge 120 and cap device 130. The alignment tabs 132 arranged on the body of the cap device 130 can align with adjacent surfaces of the controller housing 210 to provide the selected orientation of the output port during operation. If, for example, the cap device 130 were joined with the pump housing 100 in an orientation that is 180-degrees off from the selected orientation, the alignment tabs 132 would receive interference from the barrel channel 211 of the controller housing 210. As such, the user would be unable to attach the pump device 100 to the controller 200, thereby indicating to the user that the cap device 130 must be reoriented to the selected position.

Still referring to FIGS. 1-3, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (not shown in FIGS. 1-3) of the pump device 100. As described in more detail below, the pump device 100 includes a drive system that causes controlled dispensation of the medicine or other fluid from the cartridge 120. In some embodiments, the drive system incrementally advances a piston rod (not shown in FIGS. 1-3) longitudinally into the cartridge 120 so that the fluid is forced out of an output end 122. The septum 121 (FIG. 1) at the output end 122 of the fluid cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system 300 (FIG. 17) of the pump device 100 causes medicine to incrementally dispense from the medicine cartridge 120.

In some embodiments, the controller device is configured to removably attach to the pump device 100 in a side-by-side arrangement. As such, the controller device 200 can be electrically connected with the pump device 100 while the controller device 200 remains outside of the pump housing 110 (and, likewise, the pump device 100 remains outside of the controller housing 210). Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable when the pump device 100 is attached with the controller device 200 (as shown in FIGS. 2-3). In this embodiment, the controller device 200 includes a controller housing structure 210 having a number of features (e.g., a barrel channel 211, a rail 212, a depression 213, and a guide channel 214*a-b* that is segmented by a release latch 215) that are configured to mate with complementary features (e.g., a barrel 111, a slider channel 112, an mating extension 113, and a segmented guide rail 114*a-b*) of the pump housing structure 110 so as to form a releasable mechanical connection (as shown, for example, in FIGS. 1 and 4-5). Such mating features of the pump housing structure 110 and the controller housing structure 210 can provide a secure connection in the previously described side-by-side arrangement. It should be understood that, in other embodiments, other features or connector devices can be used to facilitate the side-by-side mounting arrangement. These other features or connector devices may include, for example, magnetic attachment devices, mating tongues and grooves, or the like.

As shown in FIG. 1, the pump device 100 may include an electrical connector 118 (e.g., having conductive pads, pins, and the like) that are exposed to the controller device 200 and that mate with a complementary electrical connector (refer to connector 218 in FIG. 4) on the adjacent face of the controller device 200. The electrical connectors 118 and 218 provide the electrical communication between the control circuitry (refer, for example, to FIG. 15) housed in the controller device 200 and at least a portion of the drive system or other components of the pump device 100. For example, in some embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump system 10 may include a gasket 140 that provides a seal that is resistant to migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

Still referring to FIGS. 1-3, the controller device 200 includes a user interface 220 that permits a user to monitor the operation of the pump device 100. In some embodiments, the user interface 220 includes a display 222 and one or more user-selectable buttons (e.g., four buttons 224*a*, 224*b*, 224*c*, and 224*d* in this embodiment). The display 222 may include an active area in which numerals, text, symbols, images, or a combination thereof can be displayed (refer, for example, to FIG. 2). For example, the display 222 may be used to communicate a number of settings or menu options for the infusion pump system 10. In this embodiment, the user may press one or more of the buttons 224*a*, 224*b*, 224*c*, and 224*d* to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224*a*, 224*b*, 224*c*, and 224*d* of the user interface 220. For example, the user may press one or more of the buttons 224*a*, 224*b*, 224*c*, and 224*d* to change the dispensation rate of insulin or to request that a bolus of insulin be dispensed immediately or at a scheduled, later time. Also, the user can activate the illumination instrument 230 on the controller device 200 by pressing one or more buttons 224*a*, 224*b*, 224*c*, and 224*d* of the user interface 220.

The display 222 of the user interface 220 may be configured to display quick reference information when no buttons 224*a*, 224*b*, 224*c*, and 224*d* have been pressed. For example, as shown in FIG. 2, the active area of the display 222 can display the time and the date for a period of time after no button 224*a*, 224*b*, 224*c*, and 224*d* has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224*a*, 224*b*, 224*c*, or 224*d* has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224*a*, 224*b*, 224*c*, or 224*d* has been actuated (e.g., after 15 seconds or the like), and then the display 22 can enter sleep mode and become blank after a second period of time in which no button 224*a*, 224*b*, 224*c*, or 224*d* has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the user interface 220 of the controller device 200 connected to the pump device 100. Such monitoring capabilities may provide comfort to a user who may have urgent questions about the current operation of the pump device 100 (e.g., the user may be unable to receive immediate answers if wearing an infusion pump device having no user interface attached thereto).

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200, which is removably attached to the pump device 100, without the requirement of locating and operating a separate monitoring module.

In other embodiments, the user interface 200 is not limited to the display and buttons depicted in FIGS. 1-3. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Figure 4:
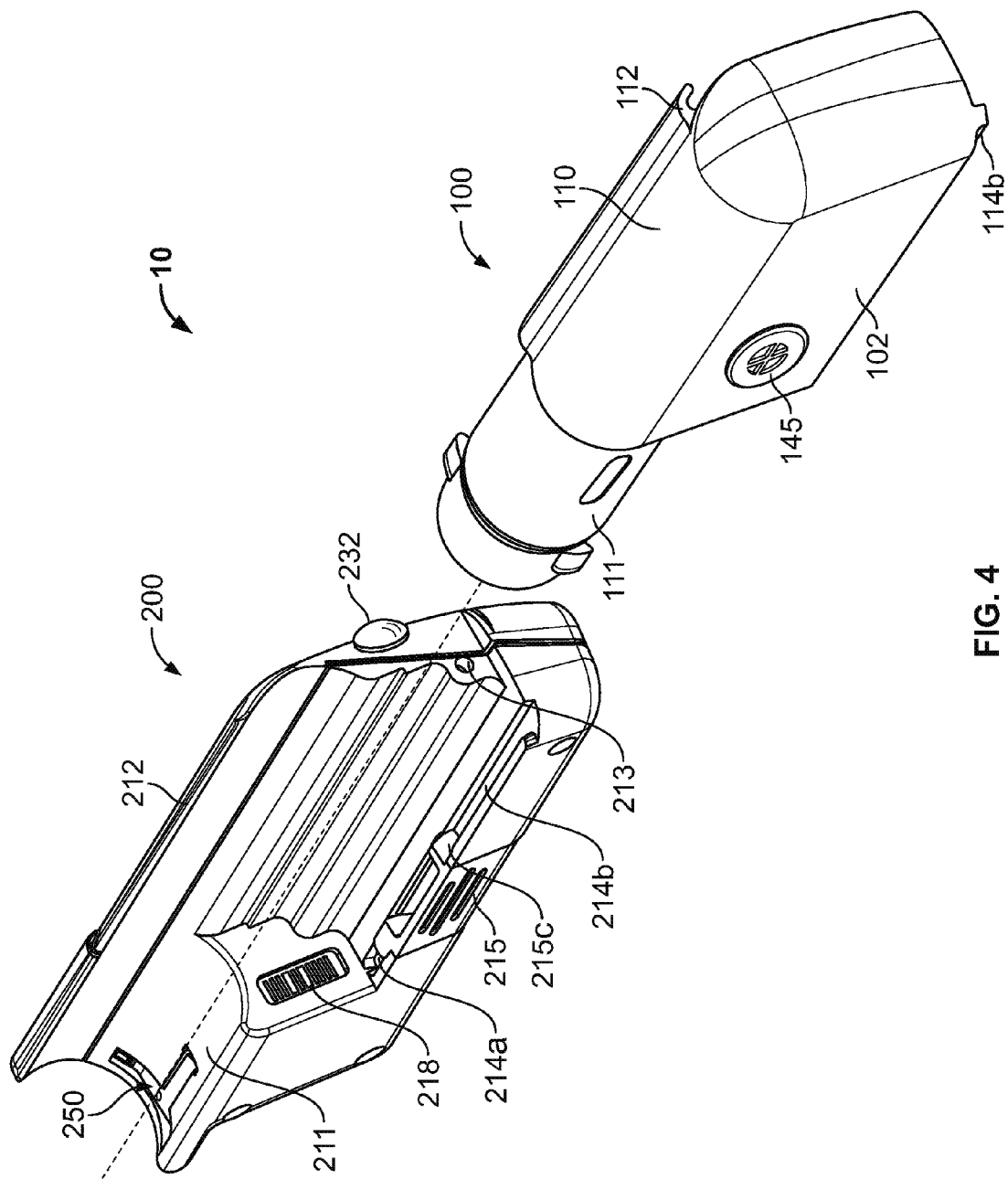
FIG. 4 is a perspective view of the infusion pump system of FIG. 1 in a detached state.
Figure 5:
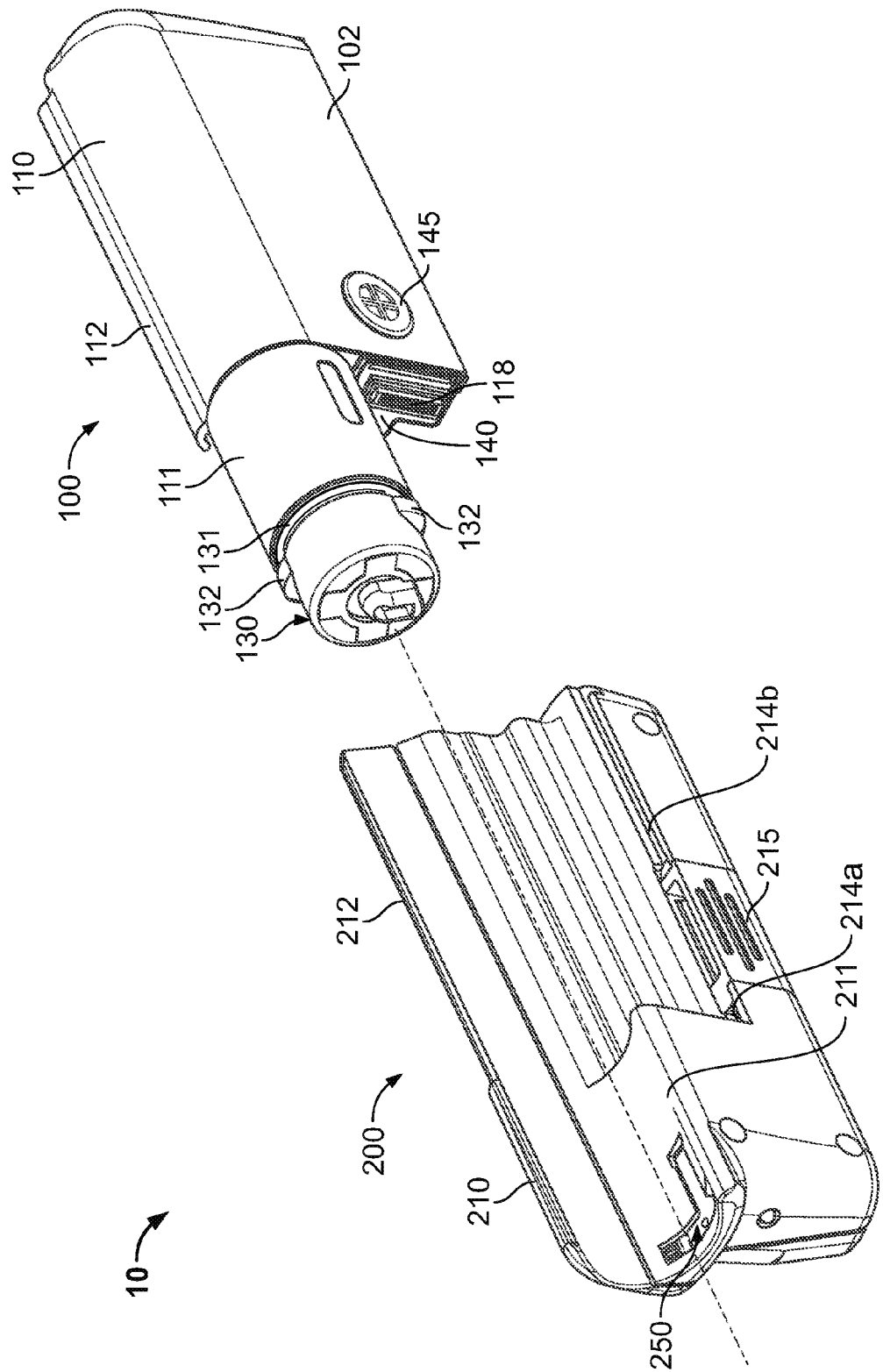
FIG. 5 is another perspective view of the infusion pump system of FIG. 4.

Referring now to FIGS. 4-5, when the infusion pump system 10 operates, the controller device 200 is removably attached to the pump device 100 in a side-by-side arrangement. For example, the pump device 100 may be moved in a longitudinal direction (e.g., refer to direction 219 in FIG. 13) toward the controller device 200 until the complementary features connect and secure the separate components in the side-by-side arrangement. In these circumstances, the pump device 100 and the controller device 200 can be separate components that fit together, but the overall size of the combined assembly is reduced because there is no requirement for one component (e.g., the controller device or pump device) to surround or envelop the second component (e.g., the pump device or controller device). Moreover, in some embodiments, the pump device 100 and controller device 200 can be readily attached together with a "one-movement" process that is convenient to the user (described in more detail below).

In this embodiment, the controller device 200 includes a controller housing structure 210 having a number of features that are configured to mate with complementary features of the pump housing structure 110 so as to form a releasable mechanical connection. For example, the pump housing structure 110 may include a barrel 111 that mates with a complementary barrel channel 211 of the controller housing 210. Also, the pump housing 110 includes slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 may include a segmented rail 114a-b (FIG. 1) that mates with a guide channel 214a-b to direct the relative longitudinal motion between the pump device 100 and the controller device 200. As described in more detail below, the segmented rails 114a-b may interact with the release member 215 so as to releasably secure the pump device 100 into assembly with the controller device 200. In addition, the pump housing 110 may include an extension 113 (FIG. 1) that mates with a depression 213 (FIG. 4) in the controller housing 210 when the pump device 100 is fully attached to the controller device 200.

Still referring to FIGS. 4-5, when the pump device 100 is advanced in the longitudinal direction toward the controller device 200 as guided by the slider channel 112 and the segmented rails 114a-b, the electrical connector 118 (FIG. 5) of the pump device 100 is directed toward engagement with the mating connector 218 (FIG. 4) of the controller device 200. As the connectors 118 and 218 join together to form the electrical connection, the release member 215 is shifted to a position between the segmented rails 114a-b so as to prevent withdrawal of the connection. Also, when the connectors 118 and 218 are mated, the extension 113 and barrel 111 are mated with the corresponding depression 213 and barrel channel 211 so as to resist relative rotational movement between the pump device 100 and the controller device 200. In this embodiment, the physical attachment of the electrical connectors 118 and 218 may also serve to resist relative rotational movement between the pump device 100 and the controller device 200. Furthermore, when the connectors 118 and 218 are mated, the slide channel 112 is mated with the corresponding rail 112 and barrel channel 211 so as to resist relative side-to-side movement between the pump device 100 and the controller device 200.

Accordingly, the pump device 100 is configured to removably attach to the controller device 200 in a manner that provides a secure fitting, an overall compact size, and a reliable electrical connection. When the pump device 100 and the controller device 200 are arranged in this side-by-side configuration, the controller device 200 can be electrically connected with the pump device 100 while the controller device 200 remains outside of the pump housing 110 (and, likewise, the pump device 100 remains outside of the controller housing 210). As such, the overall size of the assembled system 10 can be minimized, thereby providing an infusion pump system 10 having a discrete size and enhanced portability.

Additionally, in some embodiments, the attachment of the pump device 100 to the controller device 200 can be accomplished by a user with a convenient "one-movement" process. For example, as previously described, the user can readily slide the pump device 100 and the controller device 200 toward one another in a single movement (e.g., in the longitudinal direction) that causes both a physical connection and an electrical connection. As described in more detail below in connection with FIGS. 9-14, the release member 215 may be arranged so as to automatically adjust to a locked position when the pump device 100 is advanced into engagement with the controller device 200. Thus, the infusion pump system 10 permits users to readily join the pump device 100 and the controller device 200 without compound or otherwise difficult hand movements—a feature that can be beneficial to child users or to elderly users.

It should be understood that, in other embodiments, other features or connector devices can be used to facilitate the side-by-side mounting arrangement. These other features or connector devices may include, for example, magnetic attachment device, mating tongues and grooves, mounting protrusions that friction fit into mating cavities, or the like.

Still referring to FIGS. 4-5, the pump device 100 and the controller device 200 can be attached in a manner that is resistant to migration of external contaminants (e.g., water, dirt, and the like) both into the pump housing structure 110 and the controller housing structure 210. For example, when the pump device 100 is advanced in the longitudinal direction toward the controller device 200 (as guided by the slider channel 112 and the segmented rails 114a-b), the electrical connector 118 (FIG. 5) of the pump device 100 is directed toward engagement with the mating connector 218 (FIG. 4) of the controller device 200. When the connectors 118 and 218 join together to form the electrical connection, the gasket 140 is compressed between the adjacent surfaces of the pump housing 110 and the controller housing 210. The gasket 140 thereby forms a water-resistant seal between the ambient environment and the mated connectors 118 and 218.

The gasket 140 may comprise a polymer foam material that is adhered to a surface of either the pump housing 110 or the controller housing 210 (e.g., adhered to the pump housing 110 in this embodiment). The gasket 140 may be die cut to a selected shape so as to include an aperture for the electrical connection. Thus, in this embodiment, the gasket 140 surrounds the electrical connection when the pump device 100 is secured to the controller device 200. The configuration provides protection from water migration to one or both of the electrical connectors 118 and 218. Accordingly, in particular circumstances, the infusion pump system 10 can be assembled into a "water tight" configuration that protects sensitive internal components from water migration in the event that the user encounters water while wearing the pump system 10. In one example, the gasket 140 may resist migration of water to the electrical connectors 118 and 218 even when the system 10 is submerged underwater (e.g., in a pool, in a bath, or the like) for an extended period of time, such as at least 10 minutes, at least 30 minutes, at least one hour, at least two hours, and preferably at least four hours.

As shown in FIG. 5, the gasket 140 is arranged to extend generally perpendicular to the assembly motion when the pump device 100 is being attached to the controller device. For example, the pump device 100 can be attached to the controller device 200 by moving the pump device 100 in the longitudinal direction (e.g., refer to direction 219 in FIG. 13). The gasket 140 includes a major interface surface extends in a generally lateral direction that is perpendicular to the longitudinal assembly motion. Because the gasket 140 extends in a direction (e.g., the lateral direction in this embodiments) that is generally perpendicular to the attachment direction (the longitudinal direction in this embodiment), the gasket 140 can be sufficiently compressed to form a seal when the user performs the "one-movement" process to attach the pump device 100 and the controller device 200.

In addition, other paths for migration of external contaminants into the assembled pump system 10 may be sealed. For example, the pump system 10 may include one or more seals that are arranged to hinder migration of external contaminants between the cap device 130 and the pump housing 110 into the cavity 116 of the pump device 100. In this embodiment, the seal 131 arranged between the cap device 130 and the barrel 111 can provide an effective water-resistant seal against water migration into the cavity. As such, the medicine cartridge 120 and pump drive system (not shown in FIGS. 4-5) can be protected during operation.

Still referring to FIGS. 4-5, some embodiments of the infusion pump system 10 may employ a power source arranged in pump device 100 or the controller device 200 that draws upon surrounding air for optimum operation. Because the controller device 200 and the pump device 100 may be sealed to resist water migration during normal usage, a water-resistant vent instrument 145 may be used to provide the air to the power source without permitting migration of water therethrough. For example, in this embodiment, the pump device 100 may house a power source in the form of a zinc-air cell battery 345 (FIG. 17), which draws upon the surrounding air during operation. When the pump device 100 is in use, the pump housing 110 is preferably sealed to protect the internal drive system 300 (FIG. 17) and medicine cartridge from water migration. As such, the pump housing 110 may include a water-resistant vent instrument disposed proximate to the zinc-air cell battery 345 so that some air may pass through the vent and toward the battery. The water-resistant vent instrument may include one or more layers of a material that is permeable to air and resistant to passage of liquids such as water. For example, the water-resistant vent instrument may include one or more layers of a GORE-TEX material to resist the migration of water into the pump device while permitting the passage of air toward the battery.

Accordingly, the pump device 100 and the controller device 200 can be mounted to one another so that the assembled system 10 is resistant to water migration both into the pump housing structure 110 and the controller housing structure 210. Such a configuration may also provide water-resistant protection for the electrical connection between the pump device 100 and the controller 200. Thus, the sensitive internal components in the controller device 200 and the pump device 100 can be reliably protected from water migration if the user encounters water (e.g., rain, incidental splashing, and the like) while using the pump system 10.

Figure 6:
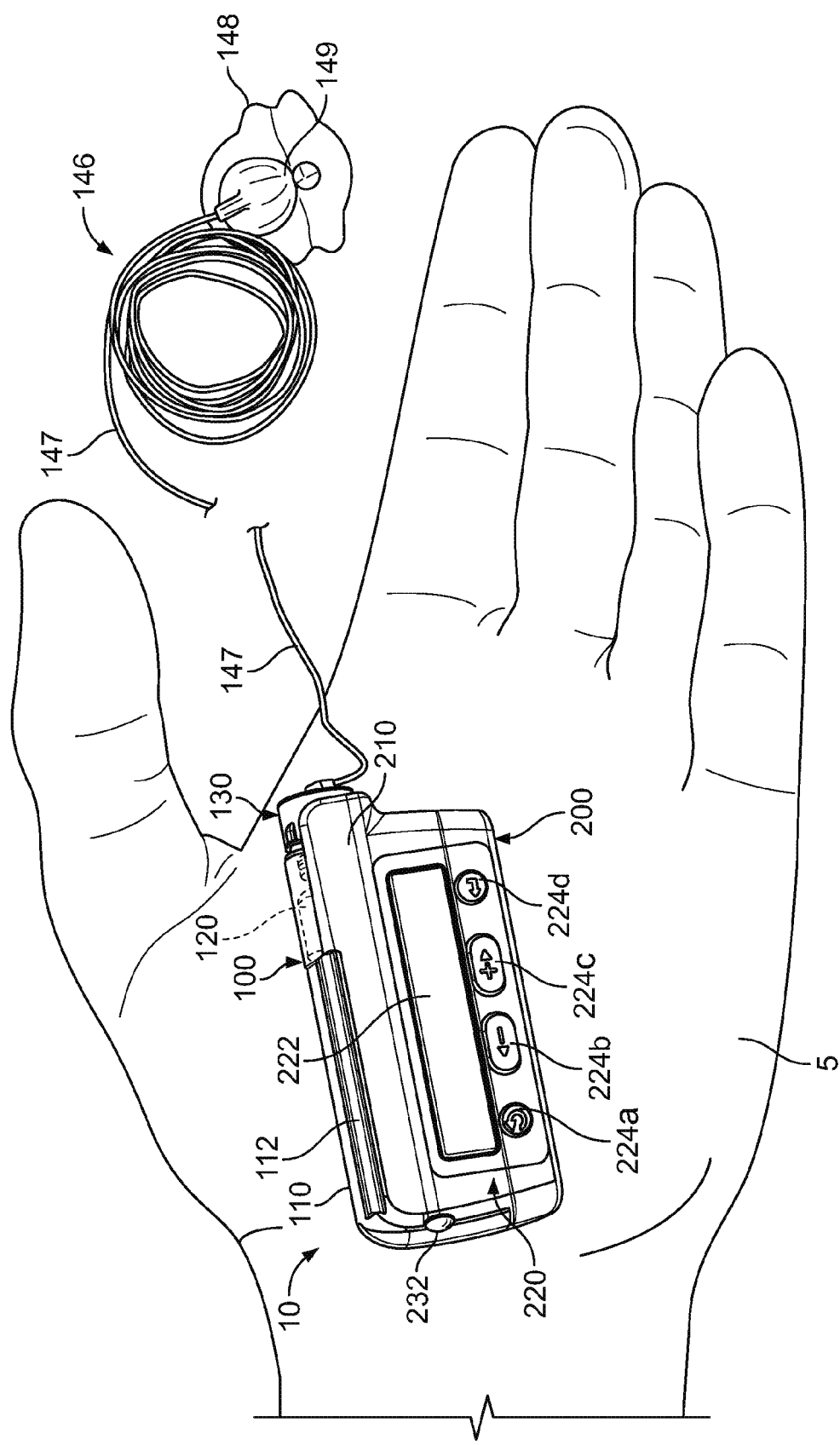
FIG. 6 is a perspective view of the infusion pump system, in accordance with some embodiments.

Referring to FIGS. 6-8, the infusion pump system 10 may be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The drive system of the pump device 100 may be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in one embodiment). In addition, the pump housing structure 110 may have an overall height of about 2 cm to about 4 cm (about 3.1 cm or less in one embodiment) and an overall thickness of about 8 mm to about 20 mm (about 17.5 mm or less in one embodiment). In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump system 10 (including the removable controller device 200 attached to the pump device 100 having the cap 130) may have an overall length of about 7 cm to about 10 cm (about 9.3 cm or less in one embodiment), an overall height of about 2 cm to about 5 cm (about 4.2 cm or less in one embodiment), and an overall thickness of about 8 mm to about 20 mm (about 17.5 mm or less in one embodiment).

The infusion pump system 10 is shown in FIG. 6 as being held in a user's hand 5 so as to illustrate an exemplary size of the system 10 in accordance with some embodiments. This embodiment of the infusion pump system 10 is compact so that the user can wear the system 10 (e.g., in the user's pocket, connected to a belt clip, adhered to the user's skin, or the like) without the need for carrying and operating a separate module. In such embodiments, the cap device 130 of the pump device 100 may be configured to mate with an infusion set 146. In general, the infusion set 146 is tubing system that connects the infusion pump system 10 to the tissue or vasculature of the user (e.g., to deliver medicine into the tissue or vasculature under the user's skin)

The infusion set 146 may include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the patient so that the medicine dispensed through the tube 147 passes through the cannula 149 and into the user's body. The cap device 130 may provide fluid communication between the output end 122 (FIG. 1) of the medicine cartridge 120 and the tube 147 of the infusion set 146. For example, the tube 147 may be directly connected to the output port 139 (FIG. 1) of the cap device 130. In another example, the infusion set 146 may include a connector (e.g., a Leur connector or the like) attached to the tube 147, and the connector can then mate with the cap device 130 to provide the fluid communication to the tube 147. In these examples, the user can carry the portable infusion pump system 10 (e.g., in the user's pocket, connected to a belt clip, adhered to the user's skin, or the like) while the tube 147 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module (refer for example to FIG. 6).

Referring to FIG. 7, in some embodiments, the infusion pump system 10 is pocket-sized so that the pump device 100 and controller device 200 can be worn in the user's pocket 6 or in another portion of the user's clothing. For example, the pump device 100 and the controller device 200 can be attached together and form the system that comfortably fits into a user's pocket 6. The user can carry the portable infusion pump system 10 and use the tube 147 of the infusion set 146 extends to direct the dispensed medicine to the desired infusion site. In some circumstances, the user may desire to wear the infusion pump system 10 in a more discrete manner. Accordingly, the user may pass the tube 147 from the pocket 6, under the user's clothing, and to the infusion site where the adhesive patch 148 is positioned. As such, the pump system 10 can be used to delivery medicine to the tissues or vasculature of the user in a portable, concealable, and discrete manner.

Referring to FIG. 8, in other embodiments, the infusion pump system 10 may be configured to adhere to the user's skin 7 directly at the location in which the skin is penetrated for medicine infusion. For example, a rear surface 102 (FIG. 3) of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 149 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220.

Referring now to FIGS. 9-14, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 9-10, the pump device 100 can be readily removed from the controller device 200 when the medicine cartridge 120 is exhausted. As previously described, the medicine cartridge 120 is inserted into the cavity 116 (FIG. 1) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length. Optionally, some embodiments of the pump device 100 may include a label 117a that is adhered around the barrel 111. The label 117a may provide a convenient location for basic user instructions, product identification information, and other information related to the infusion pump system 10. To provide enhanced viewability of the medicine cartridge 120 through the label 117a, the label 117a may include a window 117b through which the user may visually inspect if the plunger 125 is nearing the end of its travel length.

As shown in FIG. 9, the pump device 100 has been used to a point at which the medicine cartridge 120 is exhausted. The plunger 125 has been advanced, toward the left in FIG. 9, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 (and through the window 117b of the label 117a in this embodiment) to determine if the medicine cartridge 120 is almost empty. When the user determines that a new medicine cartridge 120 should be employed, the pump device 100 can be readily separated from the controller device 200 by actuating the release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 9) away from the pump device 100 (e.g., by applying a force with the user's finger).

As shown in FIG. 10, when the release member 215 is actuated and moved to a position away from the pump device 100, the segmented guide rail 114a-b is free to slide longitudinally in the guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 1) may be withdrawn from the mating depression 213 (FIG. 10), and the electrical connector 118 can be separated from the mating connector 218. In these circumstances, the pump device 100 is physically and electrically disconnected from the controller device 200 while the pump device retains the exhausted medicine cartridge 120.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., move in the lateral direction 216 in the embodiment shown in FIG. 9). Accordingly, in some embodiments, the pump device 100 can automatically and sharply move a small distance (e.g., about 0.5 mm to about 5 mm) away from the controller 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 11:
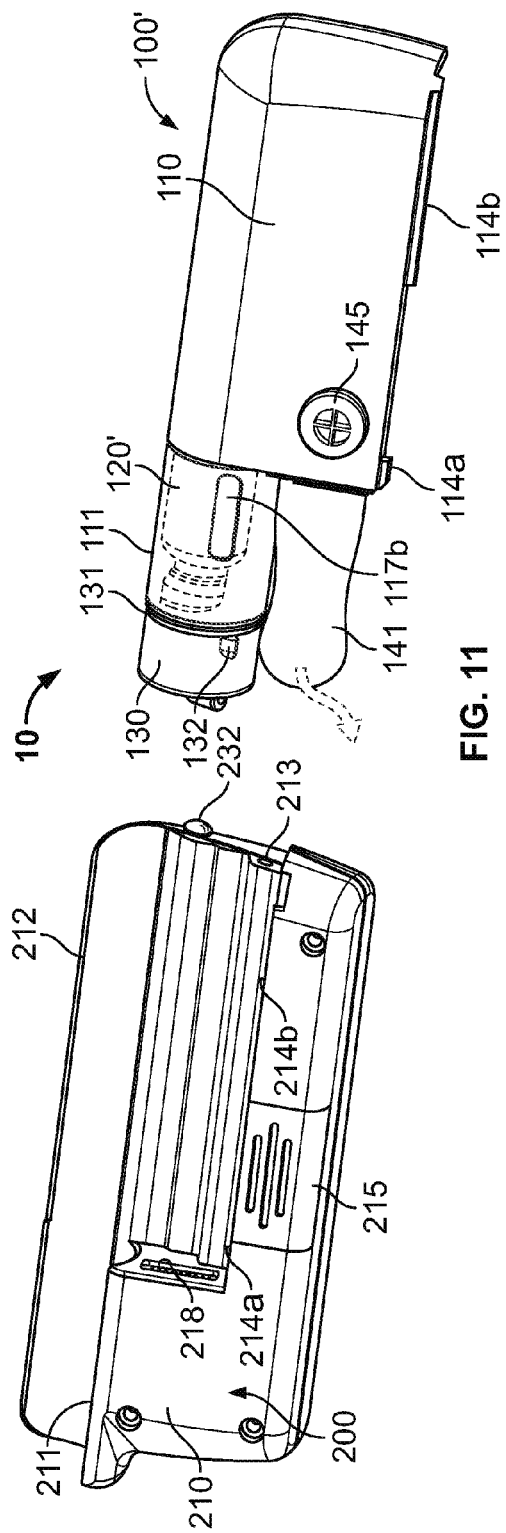
FIGS. 11 and 12 are perspective views of the pump device of FIGS. 9 and 10 being discarded and the controller device of FIGS. 9 and 10 being reused with a new pump device.
Figure 12:
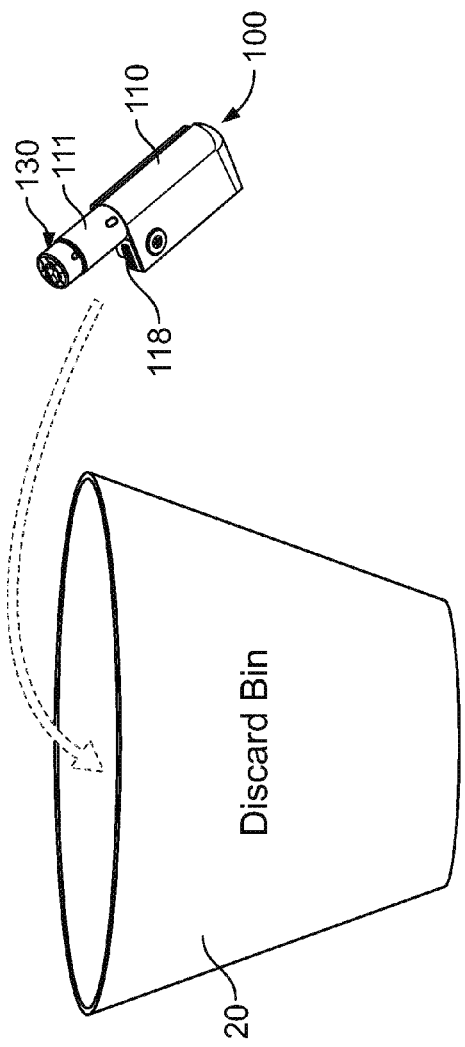

Referring to FIGS. 11-12, the same controller device 200 can be reused with a new pump device 100' having a new medicine cartridge 120' retained therein, and the previously used pump device 100 can be discarded with the exhausted medicine cartridge 120. The new pump device 100' (FIG. 11) can have a similar appearance, form factor, and operation as the previously used pump device 100 (FIGS. 9, 10 and 12), and thus the new pump device 100' can be readily attached to the controller device 200 for controlled dispensation of medicine from the new medicine cartridge 120'. In some embodiments, the user may prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 11, it should be understood that the tubing 147 may be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller 200) before attaching the infusion set patch to the user's skin. As shown in FIG. 11, the new medicine cartridge 120' may be filled with medicine such that the plunger 125 is not viewable through the barrel 111.

As shown in FIG. 12, the previously used pump device 100 that was separated from the controller device 200 (as described in connection with FIGS. 9-10) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 20, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 146 (not shown in FIG. 12, refer to FIG. 6) that was used with the pump device 100 may be removed from the user and discarded into the bin 20 along with the pump device 100. Alternatively, the infusion set 146 can be disconnected from the previous pump device 100 and attached to the new pump device 100'. In these circumstances, the user may detach the infusion set cannula and patch from the skin so as to "re-prime" the tubing with medicine from the new pump device 100' to remove air pockets from the tubing. Thereafter, the infusion set cannula and patch can be again secured to the user's skin.

Referring to FIGS. 13-14, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling the removable tab 141 away from the pump housing 110. In this embodiment, the new pump device 100' includes the removable tab 141 to seal the battery in the unused pump device 100' and thereby maintain the battery in a storage mode (refer, for example, to FIG. 12 in which the removable tab 141 is arranged to cover an internal face of the vent 115). As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

The pump device 100' can be connected to the controller device 200 by advancing the pump device 100' in a longitudinal direction 219 (FIG. 13) toward the controller device 200. When the pump device 100' is advanced in the longitudinal direction 219 toward the controller device 200, the movement is guided by the slider channel 112 (FIGS. 4-5) and the segmented rails 114a-b. In particular, the slider channel 112 of the pump housing engages the rail 212 of the controller housing 210. Also, the front portion of the segmented rail 114a slides into the rear portion of the guide channel 214b. In this embodiment, the front portion of the segmented rail 114a includes a ramp surface 114c (refer also to FIG. 1) that engages a complementary ramp surface 215c (FIG. 4) of the release member 215 to thereby force the release member 215 away from the guide channel 214a-b during advancement of the pump device 100'. The release member 215 is temporarily forced away from the guide channel 214a-b so that the front portion of the segmented rail 114a passes over the release member 215, which enables the electrical connector 118 of the pump device 100' to engage with the mating connector 218 of the controller device 200. As the connectors 118 and 218 join together to form the electrical connection, the release member 215 biased to return to its latched position and is shifted to a position in the guide channel 214a-b between the segmented rails 114a-b so as to prevent withdrawal of the pump device 100'.

Also, when the connectors 118 and 218 are mated, the extension 113 (FIG. 1) and barrel 111 are mated with the corresponding depression 213 and barrel channel 211 so as to resist relative rotational movement between the pump device 100 and the controller device 200. In this embodiment, the physical attachment of electrical connectors 118 and 218 may also serve to resist relative rotational movement between the pump device 100 and the controller device 200. Furthermore, when the connectors 118 and 218 are mated, the slide channel 112 is mated with the corresponding rail 112 (FIG. 1) and barrel channel 211 so as to resist relative side-to-side movement between the pump device 100 and the controller device 200.

As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 permits users to readily join the pump device 100' and the controller device 200 without compound or otherwise difficult hand movements—a feature that can be beneficial to child users or to elderly users.

As shown in FIG. 14, when the pump device 100' is fully advanced and attached to the controller device 200, the gasket 140 is compressed between the opposing surfaces of the pump housing 110 and the controller housing 210. Such a configuration provides a water-resistance seal around the electrical connection that protects the sensitive internal components of the pump device 100' and the controller device 200 from damage or malfunction. Although the tubing 147 of the infusion set 146 is not shown in FIGS. 13-14, it should be understood that the tubing 147 may be attached to the cap device 130 to provide a fluid path from the new pump device 100' to the user.

Accordingly, the pump device 100' can removably attach to the controller device 200 in a manner that provides a secure fitting, an overall compact size, and a reliable electrical connection. When the pump device 100' and the controller device 200 are arranged in this side-by-side configuration, the controller device 200 can be electrically connected with the pump device 100' while the controller device 200 remains outside of the pump housing 110 (and, likewise, the pump device 100 remains outside of the controller housing 210). As such, the overall size of the system 10 can be minimized, thereby providing an infusion pump system having a discrete size and enhanced portability.

Figure 15:
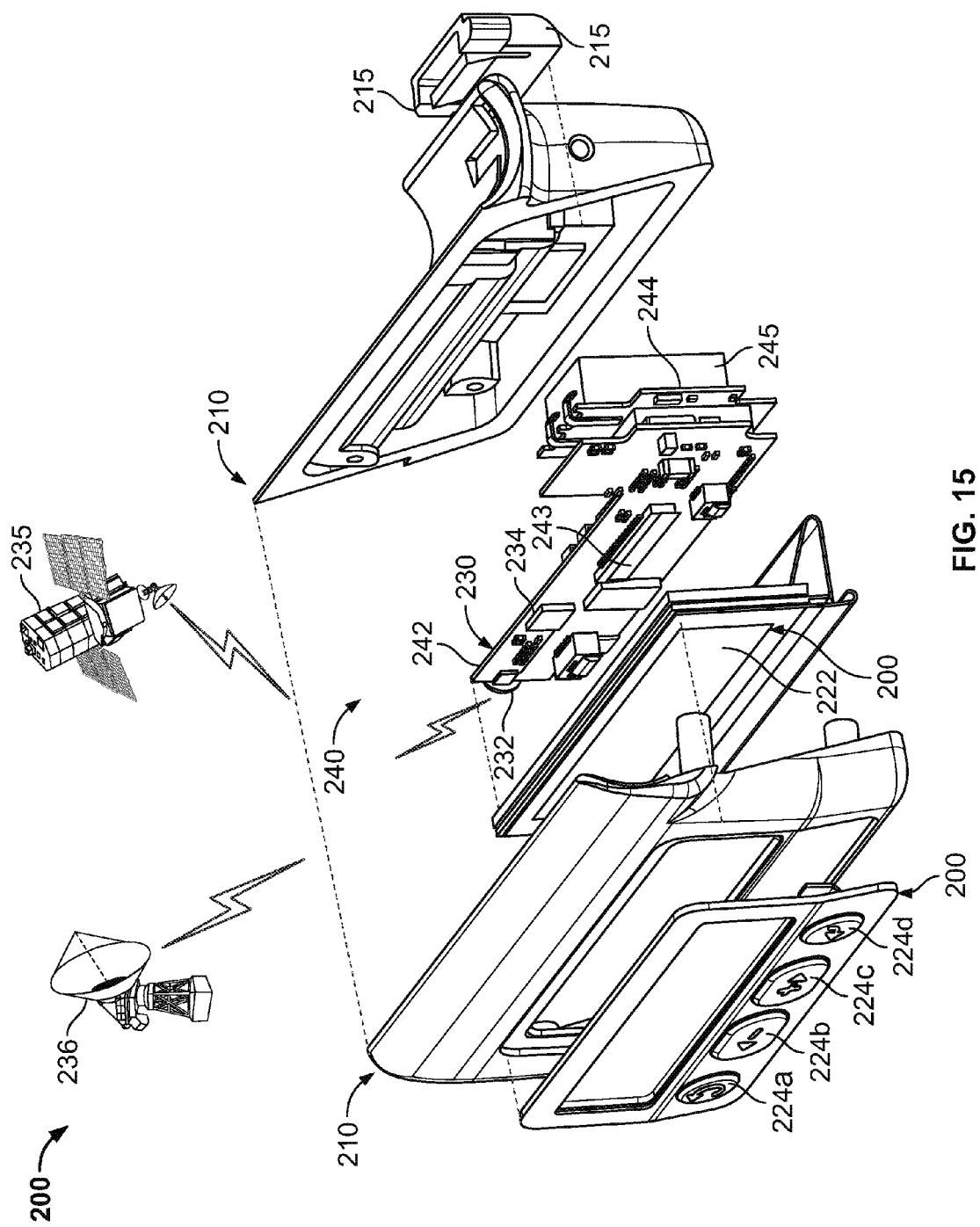
FIG. 15 is an exploded perspective view of a controller device for an infusion pump system, in accordance with some embodiments.

Referring now to FIG. 15, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the system 10. Such settings may be stored in the memory devices arranged in the control circuitry 240. Furthermore, the control circuitry 240 may include one or more dedicated memory devices that store executable software instructions for the processor 243. The control circuitry 240 may include other components, such as sensors, that are electrically connected to the main processor board 242. For example, at least a portion of the occlusion sensor 250 (not shown in FIG. 15) can be electrically connected to the main processor board 242 via a flexible circuit substrate or one or more wires.

Still referring to FIG. 15, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of settings or menu options for the system 10. In this embodiment, the control circuitry 240 may receive the input commands from the user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port or another data cable port) that is accessible on an external portion of the controller housing 210. As such, a cable may be connected to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable may also provide recharging power.

Still referring to FIG. 15, the control circuitry 240 of the controller device 200 may include a second power source 245 that can receive electrical energy from a first power source 345 (FIG. 17) housed in the pump device 100. In this embodiment, the second power source 245 is coupled to the power supply board 244 of the control circuitry 240. The hard-wired transmission of the electrical energy can occur through the previously described connectors 118 and 218 (FIGS. 4-5). In such circumstances, the first power source 345 (FIG. 17) may include a high density battery that is capable of providing a relatively large amount of electrical energy for its package size, while the second power source 245 (FIG. 15) may include a high current-output battery that is capable discharging a brief current burst to power the drive system 300 of the pump device 100. Accordingly, the first battery 345 (FIG. 17) disposed in the pump device 100 can be used to deliver electrical energy over time (e.g., "trickle charge") to the second battery 245 when the controller device 200 is removably attached to the pump device 100. For example, as previously described, the first battery 345 (FIG. 17) may comprise a zinc-air cell battery. The zinc-air cell battery may have a large volumetric energy density compared to some other battery types. For example, the zinc-air cell battery may have a volumetric energy density of greater than about 900 Watt-hours/Liter (Wh/L), about 1000 Wh/L to about 1700 Wh/L, and about 1200 Wh/L to about 1600 Wh/L. Also, the zinc-air cell battery may have a long storage life, especially in those embodiments in which the battery is sealed (e.g., by the removable tab 141 or the like) during storage and before activation. One exemplary zinc-air cell battery provides a potential voltage of about 1.1V to about 1.6V (about 1.2V to about 1.4 V, and about 1.3 V in one embodiment), a current output of about 8 mA to about 12 mA (about 10 mA in one embodiment), and a storage capacity of greater than about 600 mA·h (about 650 mA·h in one embodiment).

As shown in FIG. 15, the second battery 245 may include a high current-output device that is housed inside the controller housing 210. The second battery 245 can be charged over a period of time by the first battery 345 (FIG. 17) and then intermittently deliver high-current bursts to the drive system 300 over a brief moment of time. For example, the second battery 245 may comprise a lithium-polymer battery. The lithium polymer battery disposed in the controller device 200 may have an initial current output that is greater than the zinc-air cell battery disposed in the pump device 100, but zinc-air cell battery may have an energy density that is greater than the lithium polymer battery (e.g., the lithium polymer battery disposed in the controller device 200 may have a volumetric energy density of less than about 600 Wh/L). In addition, the lithium-polymer battery 245 is readily rechargeable, which permits the zinc-air battery disposed in the pump device 100 to provide electrical energy to the lithium-polymer battery 245 for purposes of recharging. One exemplary lithium-polymer battery provides a initial current output of about greater than 80 mA (about 90 mA to about 110 mA, and about 100 mA in one embodiment) and a maximum potential voltage of about 4.0V to and 4.4V (about 4.2 V in one embodiment). In other embodiments, it should be understood that the second power source 245 may comprise a capacitor device capable of being recharged over time and intermittently discharging a current burst to activate the drive system 300.

Accordingly, the infusion pump system 10 having two power sources 245, 345, one arranged in the pump device 100 and another arranged in the reusable controller device 200, permits a user to continually operate the controller device 200 without having to recharge a battery via a wall-plug or other cable. Because the controller device 200 can be reusable with a number of pump devices 100 (e.g., attach the new pump device 100' after the previous pump device 100 is expended and disposed), the second power source 245 in the controller device 200 can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Still referring to FIG. 15, the control circuitry 240 includes an external reference system 230 having a receiver 232 and an external reference circuitry 234. The receiver 232 communicates with the external reference circuitry 234 and receives a signal indicative of a time, a date, or both from a remote time and date reference source 235 (or 236). For example, the remote time and date reference source 235 (or 236) may include a radio transmitter, a satellite, a cellular telephone tower, or other signal broadcasting source. As explained in further detail below, the remote reference source 235 (or 236) broadcasts a reference signal that may be contemporaneously broadcasted or otherwise transmitted to multiple devices including, but not limited to, the portable medical devices, such as the infusion pump system 10, described herein. Thus, in these embodiments, the broadcast signal is not necessarily transmitted exclusively to a targeted device, but can be transmitted over a broad geographical area and can be received by more than one device (e.g., the infusion pump system 10, other medical devices, cell phones, GPS monitor devices, radio devices, and others).

In this embodiment, the receiver 232 is illustrated as extending to a region along the controller housing 210. In alternative embodiments, the receiver 232 can be fully housed within the controller housing 210. In response to receiving the broadcast signal indicative of the time/date from the remote time and date reference source 235 (or 236), the receiver 232 sends a corresponding signal to the external reference circuitry 234. The external reference circuitry 234 processes the signal and sends a time/date update signal to the processor 243 of the control circuitry 240, which regulates operation of the infusion pump system 10 based thereon. The processor 243 can include an internal reference circuitry, which is automatically updated based on the time/date update signal.

This automatic update may occur at predetermined events. For example, the automatic update may occur upon replacement of a battery, at regularly scheduled intervals (e.g., every 5, 10, 15, 30 minutes, every hour, every few hours, twice daily, once daily, as a few examples). In alternative embodiments, the automatic update may occur continuously.

The external reference system 230 enables the infusion pump system 10 (FIG. 1) to have an internally stored reference time that is updated by an external time signal. The external time signal may include a broadcast signal generated by a radio clock transmitter, a cellular telephone system and/or a global positioning system (GPS). In this manner, an accurate reference time for the infusion pump system 10. By updating and maintaining the internal time and date settings, the pump system 10 may provide the basal delivery of medicine at the correct times according to the predetermined delivery schedule. Furthermore, the system may include computer-readable memory in the controller device 200 that can record dispensation data and other data along with accurate time-stamps that are based on the updated time and date information. Accordingly, some medical decisions, which are based on a review of pumping details, can be made with confidence knowing that the time and date information was accurate when it was recorded.

Still referring to FIG. 15, some embodiments of the external reference system 230 may be provided as a radio clock system, which is synchronized by a time code bit stream that is transmitted by a radio transmitter 236. The radio transmitter 236 can be coupled to a time standard, such as an atomic clock, so that the radio transmitter broadcasts a time/date signal indicative of the time standard. In the case of a radio clock system, the receiver 232 includes an antenna that receives a radio frequency (RF) time code signal, and the external reference circuitry 234 includes a receiving circuit, which converts the RF time/date code signal into a digital time/date code signal. The external reference circuitry 234 or another component of the control circuitry 240 can decode the digital code signal and outputs a time/date signal. For example, in the case of a radio clock system, the remote time and date reference source can include one or more of the following:

U.S. NIST (National Institute of Standards and Technology) broadcasts
    U.S. Longwave radio station WWVB at 60 kHz and 50 kW
    U.S. Shortwave radio station WWV at 2.5, 5, 10, 15 and 20 MHz and 2.5-10 kW
    U.S. Shortwave radio station WWVH at 2.5, 5, 10 and 15 MHz and 2.5-10 kW
    German broadcasts from DCF77 (Mainflingen) at 77.5 kHz Canadian broadcasts from CHU (Ottawa) at 3.33, 7.335 and 14.67 MHz UK broadcasts from MSF (an atomic clock near Rugby) at 60 kHz Japanese broadcasts from BY radio stations at 40/60 kHz Chinese broadcasts from the BPM radio station (Xi'an) at 2.5, 5, 10 and 15 MHz Swiss Broadcasts from the HBG longwave transmitter (Prangins) at 75 kHz French broadcasts from radio station TDF (Allouis) at 162 kHz In another embodiment, the external reference system 230 may be configured to receive a GPS clock signal that is transmitted from a GPS satellite 235 or other satellite. The GPS clock system combines time estimates from multiple satellite atomic clocks with error estimates maintained by a network or ground stations. Because GPS clocks simultaneously compute the time and position from several sources, they can automatically compensate for line-of-sight delay and many radio propagation defects. Furthermore, GPS clocks may achieve sub-microsecond precision under ideal conditions. The GPS clock provides sufficient accuracy in that the displayed time will be accurate to approximately one half of a second, which can be adequate for medical device purposes. The GPS clock system may operate with one or more of a GPS satellite, a Galileo satellite and a GLONASS (Global Navigation Satellite System). These satellite navigation systems have a caesium or rubidium atomic clock on each satellite, reference to a clock or clocks on the Earth. Some navigation units can serve as local time standards, with a precision of about one microsecond (IS).

In still another embodiment, the external reference source 235 may include a cellular telephone time signal (e.g., from one or more cellular towers, from a cellular base station, or from a cellular satellite). In an exemplary embodiment, a CDMA (code division multiple access) clock may be implemented, which include high quality standard time signals.

In other embodiments, the externals reference source 235 can include a computer, such as a desktop computer or a laptop computer. The pump device 100 can be coupled to the computer to electronically communicate with the computer. This can be achieved using a wired connection or a wireless connection, such as a Bluetooth connection, between the pump device 100 and the computer. The external time reference can be provided using the network time protocol (NTP) of a network, of which the computer is a part. NTP functions to synchronize the clocks of computers over a network By coupling the pump device 100 to the computer, the pump device 100 can function as an extension of the network and the time reference of the pump device 100 can by synchronized like that of other components of the network. It is also anticipated that the pump device 100 can directly communicate with an NTP server or a National Institute of Standards and Technology (NIST) server, either of which can provide the external time reference.

The external reference system 230 may provide a number of advantages when implemented in a medical device, such as the previously described pump system 10. For example, the external reference system 230 can be used to maintain accurate time and date information even in the event of a power interruption. In particular, when the power is removed during a battery change and/or the battery depletes over time, the internal reference time can be affected. After the power is replaced, the external reference system 230 can communicate with the remote time and date reference source 235, 236 to accurately update the internal reference time and date. In this manner, the external reference system 230 can reduce the risk of the reference time either not being updated or not being accurately updated by the user. Furthermore, the accuracy of the internal reference time can be maintained throughout the operation of the medical device.

Some of these advantages are particularly highlighted in the case where the medical device includes an insulin pump system, such as the portable infusion pump system 10 described in connection with FIGS. 1-3. More specifically, the insulin pump system 10 can provide time-based dosing of basal insulin. As such, the basal dosing rate may be adjusted by the controller device 200 based on the particular time of day. For example, the dosing rate can be set at one level early in the morning, when the user is first awakening. The controller device 200 may automatically adjust the dosing rate to a different level at mealtimes or in the evening, for example. Accordingly, the external reference system 230 provides an accurate time setting to ensure that the dosing rate is appropriate for the time of day.

In some cases, a user may suspend or otherwise take a break from treatment, which may lead the user to remove the power supply from the medical device (e.g., to render alarms inactive). In such circumstances, the internal reference time may become inaccurate when the medical device is reactivated. The external reference system 230 can resolve this inaccuracy by enabling the internal reference time to be automatically updated based on the external reference signal from the remote time and date reference source 235, 236. Thus, the use of the medical device can be simplified, because the user is not required to manually set the time and date. Furthermore, the documentation, such as an instruction manual, which accompanies the medical device, may be simplified. For example, instructions on how to manually set the time and date may not be required.

Figure 16:
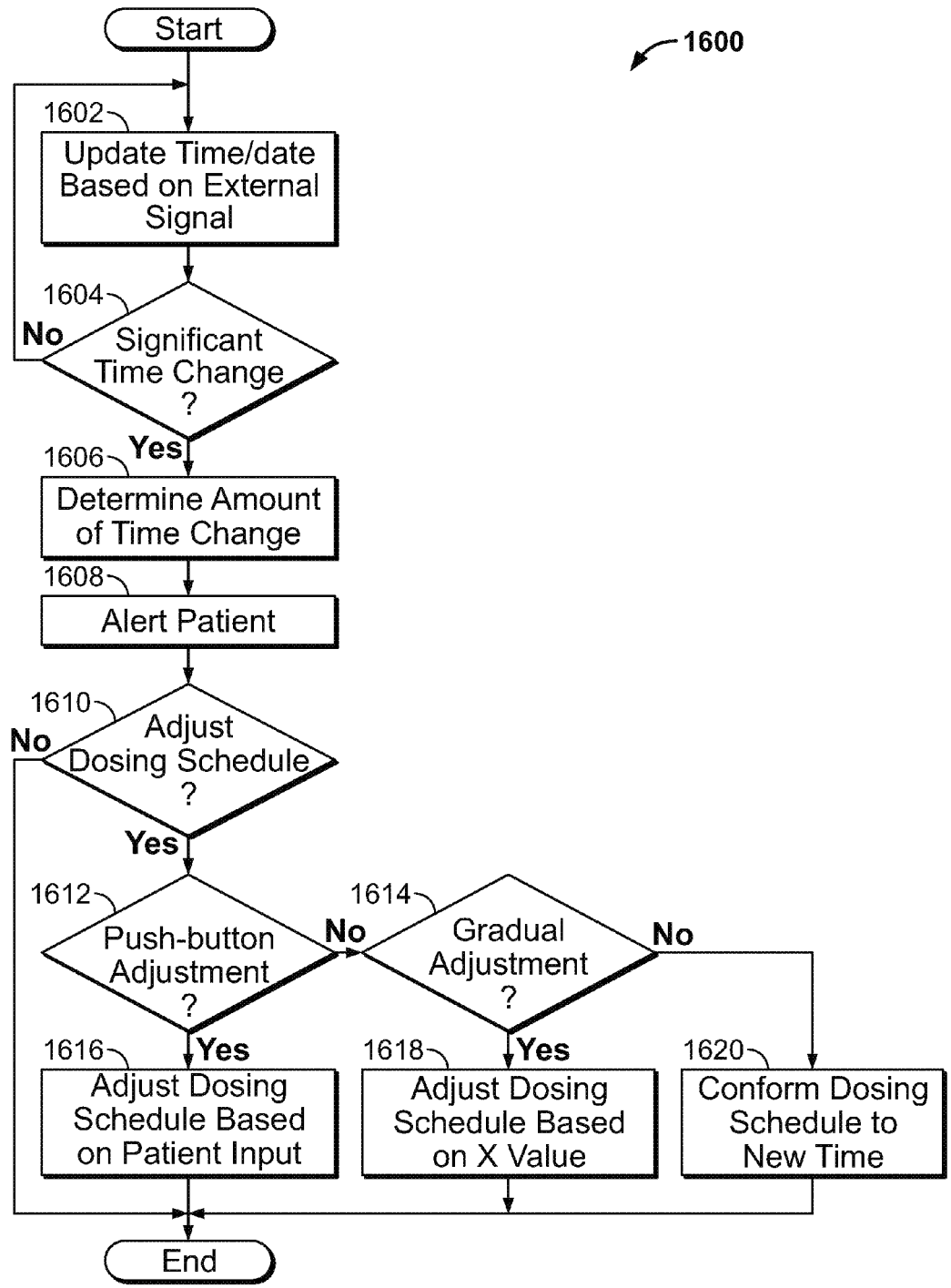
FIG. 16 is a flowchart illustrating automatic time and date setting and maintenance in accordance with an exemplary embodiment.

Referring to FIG. 16, the external reference system 230 can also be implemented to automatically adjust the dosing schedule in the case of a time change. In one example, at certain times of the year, the local time of a particular location may increase or decrease to account for daylight savings time. In other instances, a user may travel between time zones, where the time change can be several hours or even an entire day. The external reference system 230 can alert the user to such time changes and assist the user in adapting the dosing schedule to the new time zone. In some instances, the time zone change may be for a brief time period, such as when a user travels out of his/her home time zone for a brief period and then returns. In such a case, the user may instruct the insulin pump system 10 to function as normal, without adjusting the dosing rate to the new time zone.

In the case where the dosing rate is to be adjusted to a time change, an adaptive time-shift learning feature can be provided. In one embodiment, the user can indicate to the insulin pump system 10 (e.g., via a button on the controller device 200), as to when the first dosing should occur. For example, when the user awakens in the morning after a time change has occurred, the user can press a button or other input to instruct the initial dosing to occur at that time. In this manner, the dosing schedule can automatically adjust based on the timing of the initial dosing. In addition or in the alternative, the user can indicate to the insulin pump system 10, as to when a mealtime (e.g., the first mealtime) is to occur after a time change. For example, when the user prepares for a meal after arriving in a new time zone or after a time change has occurred, the user may press a button or other input to alert the insulin pump system 10. In this manner, the dosing schedule may automatically adjust based on the timing of a meal.

In another embodiment, the dosing rate may be gradually adjusted based on the time change. More specifically, the dosing schedule, which is controlled by the controller device 200, may be incrementally shifted to adjust to the time change. For example, the dosing schedule may be shifted X minutes per hour until the dosing schedule corresponds with the new time. The value X can increase or decrease based on the time change. For example, the value X may be lower for a small time change than that for a larger time change. In one embodiment, the value X may be limited to avoid an overly aggressive shift.

Furthermore, the value X can be a function of the rate at which the user's internal time reference changes. More specifically, the hypothalamus gland of the user regulates certain metabolic processes and other autonomic activities. The hypothalamus also coordinates seasonal and circadian rhythms. A circadian rhythm is a roughly 24-hour cycle in the physiological processes of living beings. The value X can relate to the circadian rhythm of the user.

As an alternative embodiment, the dosing schedule, which is controlled by the controller device 200, may adjust to conform to the new time zone by making a step-shift. For example, if the user travels to a time zone that is one hour ahead/behind of the user's home time zone, the dosing schedule may step-shift one hour forward/backward, upon request of the user. The amount of the step-shift may be limited to avoid occurrences of too much or too little dosing. For example, if the step-shift would result in over- or underdosing, the user is alerted and the step-shift in the dosing schedule does not occur. In some embodiments, the user can anticipate a tome change and can initiate a dosing schedule adaptation prior to the time change. For example, the user may be preparing for a trip to a different time zone and can initiate a change in the dosing schedule prior to departing on the trip. In this manner, the effect of a time zone change can be better managed and minimized.

Referring to FIG. 16, a flowchart illustrates an exemplary adaptive time-shift learning process 1600. At step 1602, the controller device 200 updates the date and/or time based on the external reference signal transmitted from the external reference source 235, 236 to the receiver 232. At step 1604, the controller device 200 determines whether there is a significant time change. For example, a significant time change occurs when the time is shifted by at least a threshold amount (e.g., greater than about 15 minutes, greater than about 30 minutes, and about 1 hour). Exemplary significant time changes include, but are not limited to, a time change due to daylight savings time and/or a time change due to a transition between time zones. If there is no significant time change, the external reference system 230 can automatically adjust the internal reference time of the controller device 200 without any further user input, and the process 1600 can loop back to step 1602. If there is a significant time change, the exemplary adaptive time-shift learning determines the amount of the time change at step 1606.

At step 1608, the controller device 200 alerts the patient as to the time change. At step 1610, it is determined whether the dosing schedule is to be adjusted. This determination can be based on the patient's input. For example, the user may decide that no adjustment is necessary (e.g., in the case where the user has only briefly transitioned between time zones). If there is no adjustment to be made, the adaptive time-shift process ends. If an adjustment is to be made, the controller device 200 determines whether a push-button adjustment is to be made at step 1612. If no push-button adjustment is to be made, the exemplary adaptive time-shift process continues at step 1614. If a push-button adjustment is to be made, the controller device 200 adjusts the dosing schedule based on a user input at step 1616. More specifically, the dosing schedule may be adjusted based on the user indicating an initial dosing for the day and/or the user indicating a mealtime (e.g., breakfast, lunch and/or dinner), as described in further detail above.

At step 1614, the controller device 200 determines whether a gradual adjustment is to be made. If a gradual adjustment is to be made, the controller device 200 adjusts the dosing schedule based on the above-described rate (i.e., X value) at step 1618. If a gradual dosing schedule adjustment is not to be made, the controller device 200 conforms the dosing schedule to the new time. For example, the dosing schedule may step-shift forward or backward based on the new time. Such a step-shift may be limited, however, based on several factors including, but not limited to, the current dosing rate, the dosing rate after the step-shift, a recent dosing history and the like. In this manner, it may be insured that the user does not receive too much or too little insulin, for example, as a result of the step-shift.

Figure 17:
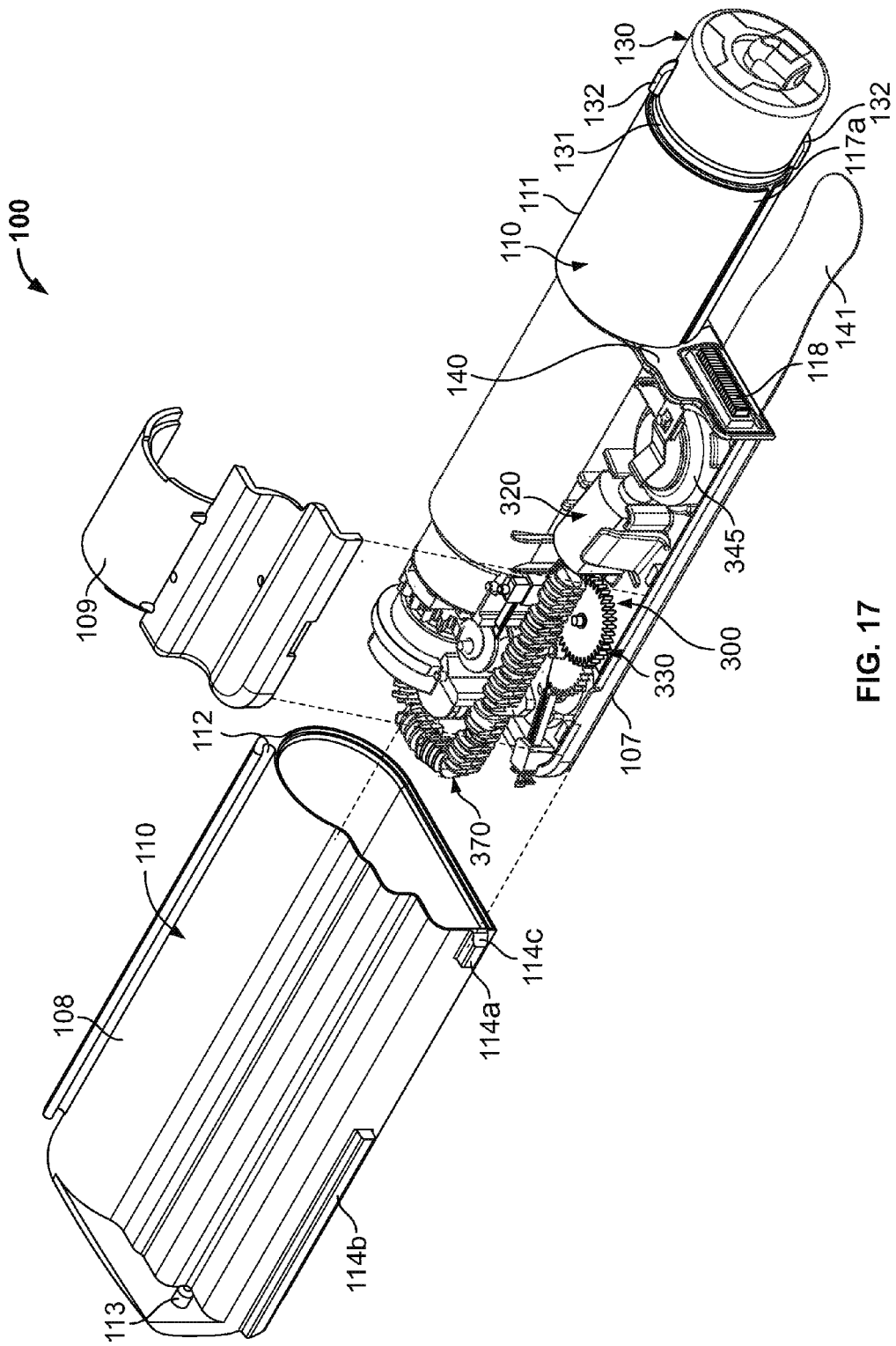
FIG. 17 is an exploded perspective view of a pump device for an infusion pump system, in accordance with some embodiments.

Referring now to FIG. 17, as previously described, the infusion pump system includes the pump device 100 having a drive system 300 controlled by the removable controller device 200 (FIGS. 1-2). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. In this embodiment, the pump housing 110 includes a chassis 107, a shell portion 108, and a cover mount 109. The shell portion 108 can be used to cover at least a portion of the drive system 300. For example, the shell 108 may include an inner curved surface against which a curved section of a piston rod 370 rests. The cover mount 109 may be assembled to the chassis 107 of the pump housing 110 to secure some components of the drive system 300 in position between the cover mount 109 and the chassis 107. When the cover mount 109 is assembled into place, the "unused" or retracted portion of the piston rod 370 may rest in a channel defined in the top of the cover mount 109. The shell portion 108 can slide over the cover mount 109 and join with the chassis 107 to form the assembled pump housing 110.

Some embodiments of the drive system 300 may include a battery powered actuator (e.g., reversible motor 320 or the like) that drives a gear system 330 to actuate a ratchet-spring mechanism and advance the flexible piston rod 370 toward the medicine cartridge 120 (as described in commonly assigned U.S. patent application Ser. No. 11/677,706 filed on Feb. 22, 2007, which is incorporated herein by reference). Accordingly, control signals from the controller device 200 can be transmitted via the electrical connector 118 so as to control the motor 320, which causes the gear system 330 and other components to actuate and thereby advance the piston rod 370 an incremental distance toward the medicine cartridge. This incremental motion urges the plunger 125 (FIG. 1) of the medicine cartridge 120 to force an incremental amount of medicine from the pump device 100. Accordingly, in response to the electrical control signals from the controller device 200, the drive system 300 of the pump device 100 causes medicine to incrementally dispense from the medicine cartridge 120 and into the targeted user.

It should be understood from the description herein that, in some embodiments, the external reference system can be arranged in medical devices other that the wearable infusion pump system 10. For example, medical devices for the treatment of diabetes that are carried or otherwise worn by the user can incorporate an external reference system configured to receive an external signal from a remote time and date reference source (e.g., a radio transmitter, a satellite, another broadcast source or the like). As such, these diabetes treatment devices (e.g., infusion pumps, glucose meters, continuous glucose monitors, and the like) can be equipped to include automatic time-setting capabilities and related maintenance features.

Figure 18:
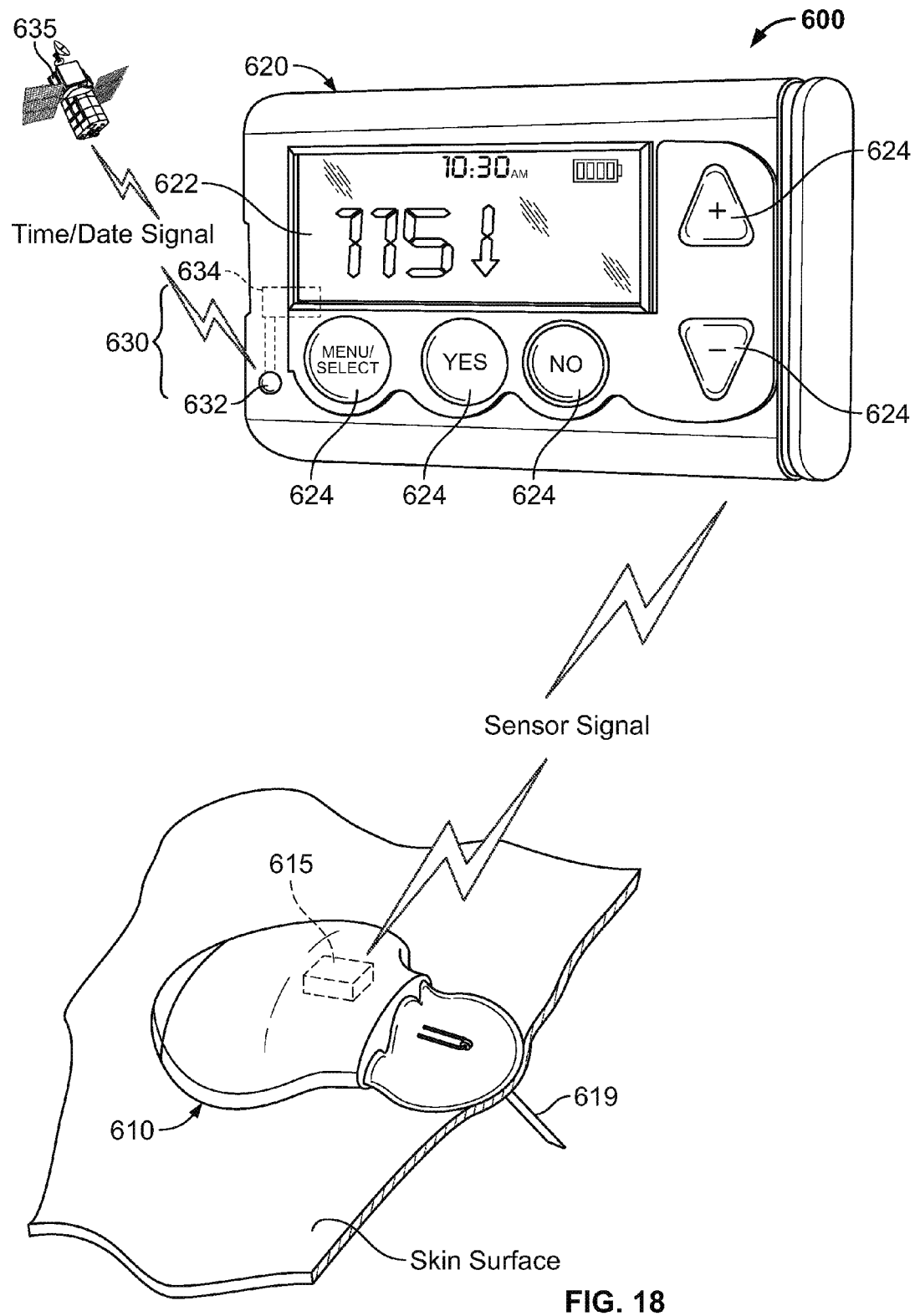
FIG. 18 is a perspective view of a continuous glucose monitoring system in accordance with some embodiments.

Referring to FIG. 18, some embodiments of a continuous glucose monitoring system 600 can be incorporate an external reference system 630 that includes a receiver 632 and external reference circuitry 634. These instruments 632 and 634 can be used to receive and decode the external reference signal that is broadcast from a remote time and date reference source 635 (e.g., a satellite, a radio transmitter, a cellular system, or another broadcast source). Similar to the previously described infusion pump system 10, the continuous glucose monitoring system 600 is configured to receive an external signal from the remote time and date reference source 635 to provide automatic time-setting capabilities and related maintenance features.

As shown in FIG. 18, the continuous glucose monitoring system 600 includes a body-worn glucose sensor device 610 that wirelessly communicates with a portable controller device 620. The glucose sensor device 610 may comprise a sensor shaft 619 that penetrates under the skin (e.g., into the subcutaneous layer) while the sensor housing is adhered to the skin. The sensor housing may contain a power source and a communication device 615 that permits the sensor data to be wirelessly transmitted to the controller device 620. The controller device 620 can include a display 622 to communicate the sensed glucose level and one or more buttons 624 for user interaction. The controller device 620 can include one or more memory devices that stored a log of the sensed glucose readings and the time and date that each reading was detected. As such, the user or a medical practitioner can perform a retrospective analysis of the user's blood glucose readings to determine if modifications should be made to the user's food consumption, physical activity, and insulin dosages.

In this embodiment, the controller device 200 includes the external reference system 630 that includes the receiver 632 and the external reference circuitry 634. The receiver 632 receives a signal indicative of a time, a date, or both from the remote time and date reference source 635. In response to receiving the broadcast signal indicative of the time/date from the remote time and date reference source 635, the receiver 632 sends a corresponding signal to the external reference circuitry 634. The external reference circuitry 634 processes the signal and sends a time/date update signal to the control circuitry of the device 620. The controller device 620 can include an internal reference circuitry, which is automatically updated based on the new time/date data from the external reference circuitry 634. This automatic update may occur at predetermined events. For example, the automatic update may occur upon replacement of a battery, at regularly scheduled intervals (e.g., every 5, 10, 15, 30 minutes, every hour, every few hours, twice daily, once daily, as a few examples). In alternative embodiments, the automatic update may occur continuously.

Still referring to FIG. 18, the external reference system 630 enables the continuous glucose monitoring system 600 to have an internally stored reference time that is updated by an external time signal. The external time signal may include a broadcast signal generated by a radio clock transmitter, a cellular telephone system and/or a global positioning system (GPS). In this manner, an accurate reference time for the continuous glucose monitoring system 600 can be maintained. This accurate reference time, for example, enables the continuous glucose monitoring system 600 to include an accurate time-stamp for each of the glucose readings that are stored in the previously described log. Because the sensor data that is collected and stored within the memory of the controller device 620 can include an associated time-stamp, the subsequent analysis of the recorded data is enhanced due to the high accuracy of the time-stamp. Accordingly, some medical decisions, which are based on a review of pumping details, can be made with confidence knowing that the time and date information was accurate when it was recorded.

It should be understood from the description herein that, in some embodiments, the external reference system can be arranged other medical devices for the treatment of diabetes. For example, a blood glucose meter device can incorporate an external reference system configured to receive an external signal from a remote time and date reference source (e.g., a radio transmitter, a satellite, another broadcast source or the like). Such a glucose meter device can be carried by a diabetic user so that the user may periodically provide a blood sample on a test strip and then insert the test blood strip into the meter device for a periodic glucose reading.

In some embodiments, the glucose meter device can include a mechanism for piercing a user's skin to allow a limited amount of blood to pass to the surface of the skin (e.g., a blood drop for the test strip). The user can apply the blood as a blood sample to a test blood strip. An end of the test blood strip, which includes the applied blood sample, can be inserted into a strip receiver of the glucose meter device. As such, the glucose meter device can test the blood sample to determine the user's current blood glucose level. The determined blood glucose level can be provided to the user visually (e.g., using a display) and/or audibly (e.g., using a speaker). Furthermore, the glucose meter device can be configured to store the glucose readings in a log (e.g., stored in one or more memory devices of the glucose meter control circuitry). These stored reading may be associated with a time stamp that indicates the time and date of the blood glucose reading. The glucose meter device can be equipped with the external reference system (as previously described) to receive a reference time and date signal and thereafter update the internal time and date settings in the control circuitry. Such an automated time updating feature can ensure that the log's time-stamp for each glucose reading is accurate, which can be beneficial to a physician or user who is performing a retrospective analysis of the user's blood glucose level throughout portions of the day or week.

Thus, a number of diabetes treatment devices (e.g., infusion pumps, glucose meters, continuous glucose monitors, and the like) can be equipped to include automatic time-setting capabilities and related maintenance features described herein.

A number of embodiments of the invention have been described. Nevertheless, it will be understood that various modifications may be made without departing from the spirit and scope of the invention. Accordingly, other embodiments are within the scope of the following claims.

What is claimed is:
1. An infusion pump system, comprising:
a disposable and non-reusable pump device including a drive system to dispense medicine from the pump device, the pump device having a first electrical connector that is externally accessible; and
a reusable controller device removably attachable to the disposable and non-reusable pump device such that the reusable controller device is mechanically mounted with the disposable and non-reusable pump device, the controller device comprising:

a second electrical connector that is engageable with the first connector to provide electrical communication between control circuitry of the controller device and the drive system of the pump device;

a user interface comprising a display device, the user interface being electrically connected to the control circuitry;

an external reference system that wirelessly receives an external reference signal indicative of a time of day from a portable computing device configured to provide short range wireless communication with the reusable controller device, the external reference system being electrically connected to the control circuitry; and a processor that updates a time setting of the infusion pump system based on the external reference signal to provide an updated time setting;

wherein the reusable controller device activates the drive system of the pump device based on the updated time setting, wherein the reusable controller device activates the drive system of the pump device according to a dispensing rate schedule based on time of day, and wherein the reusable controller device indicates a time-zone change based on the external reference signal and shifts the dispensing rate schedule based on the time-zone change.

2. An infusion pump system, comprising:

a disposable and non-reusable pump device including a drive system to dispense medicine from the pump device, the pump device having a first electrical connector that is externally accessible, wherein the disposable and non-reusable pump device comprises a pump housing that defines a space to slidably receive a medicine cartridge, wherein the disposable and non-reusable pump device includes at least one retainer structure configured to hinder removal of the medicine cartridge after exhaustion of the medicine cartridge and thereby prevent reuse of the pump device with a new medicine cartridge; and a reusable controller device removably attachable to the disposable and non-reusable pump device such that the reusable controller device is mechanically mounted with the disposable and non-reusable pump device, the controller device comprising:

a second electrical connector that is engageable with the first connector to provide electrical communication between control circuitry of the controller device and the drive system of the pump device;

a user interface comprising a display device, the user interface being electrically connected to the control circuitry;

an external reference system that wirelessly receives an external reference signal indicative of a time of day from a portable computing device configured to provide short range wireless communication with the reusable controller device, the external reference system being electrically connected to the control circuitry; and a processor that updates a time setting of the infusion pump system based on the external reference signal to provide an updated time setting;

wherein the reusable controller device activates the drive system of the pump device based on the updated time setting.

3. An infusion pump system, comprising:

a disposable and non-reusable pump device including a drive system to dispense medicine from the pump device, the pump device having a first electrical connector that is externally accessible, wherein the disposable and non-reusable pump device comprises a pump housing that has an interior cavity a space to slidably receive the medicine cartridge inserted through an external opening of the pump housing, wherein the disposable and non-reusable pump device further comprises a separate cap device configured to mate with the pump housing and cover the external opening so as to seal the medicine cartridge in the interior cavity; and a reusable controller device removably attachable to the disposable and non-reusable pump device such that the reusable controller device is mechanically mounted with the disposable and non-reusable pump device, the controller device comprising:

a second electrical connector that is engageable with the first connector to provide electrical communication between control circuitry of the controller device and the drive system of the pump device;

a user interface comprising a display device, the user interface being electrically connected to the control circuitry;

an external reference system that wirelessly receives an external reference signal indicative of a time of day from a portable computing device configured to provide short range wireless communication with the reusable controller device, the external reference system being electrically connected to the control circuitry; and a processor that updates a time setting of the infusion pump system based on the external reference signal to provide an updated time setting;

wherein the reusable controller device activates the drive system of the pump device based on the updated time setting.

4. The infusion pump system of claim 3, wherein the cap device includes a penetration member to pierce a septum of the medicine cartridge when the cap device is mated with the pump housing.

5. An infusion pump system, comprising:

a disposable and non-reusable pump device including a drive system to dispense medicine from the pump device, the pump device having a first electrical connector that is externally accessible; and a reusable controller device removably attachable to the disposable and non-reusable pump device such that the reusable controller device is mechanically mounted with the disposable and non-reusable pump device, the controller device comprising:

a second electrical connector that is engageable with the first connector to provide electrical communication between control circuitry of the controller device and the drive system of the pump device;

a user interface comprising a display device, the user interface being electrically connected to the control circuitry;

an external reference system that wirelessly receives an external reference signal indicative of a time of day from a portable computing device configured to provide short range wireless communication with the reusable controller device, the external reference system being electrically connected to the control circuitry; and a processor that updates a time setting of the infusion pump system based on the external reference signal to provide an updated time setting;

wherein the reusable controller device activates the drive system of the pump device based on the updated time setting, and wherein the user interface of the reusable controller device prompts a user to confirm that a dispensing rate schedule should be adjusted based on the updated time setting.

6. An infusion pump system, comprising:

a disposable and non-reusable pump device including a drive system to dispense medicine from the pump device, the pump device having a first electrical connector that is externally accessible; and a reusable controller device removably attachable to the disposable and non-reusable pump device such that the reusable controller device is mechanically mounted with the disposable and non-reusable pump device, the controller device comprising:
  a second electrical connector that is engageable with the first connector to provide electrical communication between control circuitry of the controller device and the drive system of the pump device;
  a user interface comprising a display device, the user interface being electrically connected to the control circuitry;
  an external reference system that wirelessly receives an external reference signal indicative of a time of day from a portable computing device configured to provide short range wireless communication with the reusable controller device, the external reference system being electrically connected to the control circuitry, wherein the external reference signal indicative of the time of day is provided from the portable computing device using a network time protocol (NTP) of a computer network that includes the portable computing device; and
  a processor that updates a time setting of the infusion pump system based on the external reference signal to provide an updated time setting;
  wherein the reusable controller device activates the drive system of the pump device based on the updated time setting.

7. The infusion pump system of claim 6, wherein the portable computing device comprises a laptop computer.

8. The infusion pump system of claim 6, wherein the portable computing device configured to provide short range wireless communication with the reusable controller device via a Bluetooth connection.

9. The infusion pump system of claim 6, wherein the reusable controller device adjusts a dispensing rate of the pump device based on the updated time setting.

10. The infusion pump system of claim 6, wherein the reusable controller device activates the drive system of the pump device according to a dispensing rate schedule based on time of day.

11. The infusion pump system of claim 10, wherein the reusable controller device indicates a time-zone change based on the external reference signal and shifts the dispensing rate schedule based on the time-zone change.

12. The infusion pump system of claim 11, wherein the dispensing rate schedule is incrementally shifted to gradually correspond to the time-zone change.

13. The infusion pump system of claim 11, wherein the dispensing rate schedule is step shifted to immediately correspond to the time-zone change.

14. The infusion pump system of claim 11, wherein the user interface queries a user to confirm whether operation of the wearable infusion pump system should be adjusted based on the time-zone change, and wherein the dispensing rate schedule shifting based on the time-zone change is only executed in response to input to the user interface.

15. The infusion pump system of claim 6, wherein the disposable and non-reusable pump device comprises a pump housing that defines a space to slidably receive a medicine cartridge, wherein the disposable and non-reusable pump device includes at least one retainer structure configured to hinder removal of the medicine cartridge after exhaustion of the medicine cartridge and thereby prevent reuse of the pump device with a new medicine cartridge.

16. The infusion pump system of claim 6, wherein the disposable and non-reusable pump device comprises a pump housing that has an interior cavity a space to slidably receive the medicine cartridge inserted through an external opening of the pump housing, wherein the disposable and non-reusable pump device further comprises a separate cap device configured to mate with the pump housing and cover the external opening so as to seal the medicine cartridge in the interior cavity.

17. The infusion pump system of claim 16, wherein the cap device includes a penetration member to pierce a septum of the medicine cartridge when the cap device is mated with the pump housing.

18. The infusion pump system of claim 6, wherein the user interface of the reusable controller device prompts a user to confirm that a dispensing rate schedule should be adjusted based on the updated time setting.

19. The infusion pump system of claim 5, wherein the portable computing device comprises a laptop computer.

20. The infusion pump system of claim 5, wherein the portable computing device configured to provide short range wireless communication with the reusable controller device via a Bluetooth connection.

21. The infusion pump system of claim 5, wherein the portable computing device is connected to a computer network having a network time protocol (NTP), and wherein the external reference signal indicative of the time of day is provided from the portable computing device via the NTP of the computer network.

22. The infusion pump system of claim 5, wherein the reusable controller device activates the drive system of the pump device according to a dispensing rate schedule based on time of day.

23. The infusion pump system of claim 22, wherein the reusable controller device indicates a time-zone change based on the external reference signal and shifts the dispensing rate schedule based on the time-zone change.

24. The infusion pump system of claim 23, wherein the dispensing rate schedule is incrementally shifted to gradually correspond to the time-zone change.

25. The infusion pump system of claim 23, wherein the dispensing rate schedule is step shifted to immediately correspond to the time-zone change.

26. The infusion pump system of claim 23, wherein the user interface queries a user to confirm whether operation of the wearable infusion pump system should be adjusted based on the time-zone change, and wherein the dispensing rate schedule shifting based on the time-zone change is only executed in response to input to the user interface.

27. The infusion pump system of claim 5, wherein the disposable and non-reusable pump device comprises a pump housing that defines a space to slidably receive a medicine cartridge, wherein the disposable and non-reusable pump device includes at least one retainer structure configured to hinder removal of the medicine cartridge after exhaustion of the medicine cartridge and thereby prevent reuse of the pump device with a new medicine cartridge.

28. The infusion pump system of claim 5, wherein the disposable and non-reusable pump device comprises a pump housing that has an interior cavity a space to slidably receive the medicine cartridge inserted through an external opening of the pump housing, wherein the disposable and non-reusable pump device further comprises a separate cap device configured to mate with the pump housing and cover the external opening so as to seal the medicine cartridge in the interior cavity.

29. The infusion pump system of claim 28, wherein the cap device includes a penetration member to pierce a septum of the medicine cartridge when the cap device is mated with the pump housing.

30. The infusion pump system of claim 3, wherein the portable computing device comprises a laptop computer.

31. The infusion pump system of claim 3, wherein the portable computing device configured to provide short range wireless communication with the reusable controller device via a Bluetooth connection.

32. The infusion pump system of claim 3, wherein the reusable controller device activates the drive system of the pump device according to a dispensing rate schedule based on time of day.

33. The infusion pump system of claim 32, wherein the reusable controller device indicates a time-zone change based on the external reference signal and shifts the dispensing rate schedule based on the time-zone change.

34. The infusion pump system of claim 33, wherein the dispensing rate schedule is incrementally shifted to gradually correspond to the time-zone change.

35. The infusion pump system of claim 33, wherein the dispensing rate schedule is step shifted to immediately correspond to the time-zone change.

36. The infusion pump system of claim 33, wherein the user interface queries a user to confirm whether operation of the wearable infusion pump system should be adjusted based on the time-zone change, and wherein the dispensing rate schedule shifting based on the time-zone change is only executed in response to input to the user interface.

37. The infusion pump system of claim 3, wherein the disposable and non-reusable pump device comprises a pump housing that defines a space to slidably receive a medicine cartridge, wherein the disposable and non-reusable pump device includes at least one retainer structure configured to hinder removal of the medicine cartridge after exhaustion of the medicine cartridge and thereby prevent reuse of the pump device with a new medicine cartridge.

38. The infusion pump system of claim 2, wherein the portable computing device comprises a laptop computer.

39. The infusion pump system of claim 2, wherein the portable computing device configured to provide short range wireless communication with the reusable controller device via a Bluetooth connection.

40. The infusion pump system of claim 2, wherein the reusable controller device activates the drive system of the pump device according to a dispensing rate schedule based on time of day.

41. The infusion pump system of claim 40, wherein the reusable controller device indicates a time-zone change based on the external reference signal and shifts the dispensing rate schedule based on the time-zone change.

42. The infusion pump system of claim 41, wherein the dispensing rate schedule is incrementally shifted to gradually correspond to the time-zone change.

43. The infusion pump system of claim 41, wherein the dispensing rate schedule is step shifted to immediately correspond to the time-zone change.

44. The infusion pump system of claim 41, wherein the user interface queries a user to confirm whether operation of the wearable infusion pump system should be adjusted based on the time-zone change, and wherein the dispensing rate schedule shifting based on the time-zone change is only executed in response to input to the user interface.

45. The infusion pump system of claim 1, wherein the portable computing device comprises a laptop computer.

46. The infusion pump system of claim 1, wherein the portable computing device configured to provide short range wireless communication with the reusable controller device via a Bluetooth connection.

47. The infusion pump system of claim 1, wherein the dispensing rate schedule is incrementally shifted to gradually correspond to the time-zone change.

48. The infusion pump system of claim 1, wherein the dispensing rate schedule is step shifted to immediately correspond to the time-zone change.

49. The infusion pump system of claim 1, wherein the user interface queries a user to confirm whether operation of the wearable infusion pump system should be adjusted based on the time-zone change, and wherein the dispensing rate schedule shifting based on the time-zone change is only executed in response to input to the user interface.

* * * * *